(12) United States Patent
Sun et al.

(10) Patent No.: US 7,544,512 B2
(45) Date of Patent: Jun. 9, 2009

(54) METHOD OF PRODUCING INSULINOTROPIC GLP-1 (7-36) POLYPEPTIDE AND/OR GLP-1 ANALOGS

(75) Inventors: Yukun Sun, Shanghai (CN); Dengxi Wu, Shanghai (CN); Aizhen Wu, Shanghai (CN); Zhiyong Zhu, Shanghai (CN); Gang Yu, Shanghai (CN); Jiaxiang Zhou, Shanghai (CN); Shaoling Zhao, Shanghai (CN)

(73) Assignee: Shanhai Hua Yi Bio-Tech Lab (CN)

( * ) Notice: Subject to any disclaimer, the term of this patent is extended or adjusted under 35 U.S.C. 154(b) by 246 days.

(21) Appl. No.: 10/761,717

(22) Filed: Jan. 20, 2004

(65) Prior Publication Data

US 2004/0146985 A1    Jul. 29, 2004

Related U.S. Application Data

(63) Continuation-in-part of application No. PCT/CN02/00502, filed on Jul. 17, 2002.

(30) Foreign Application Priority Data

Jul. 19, 2001    (CN)    ................ 01 1 26278

(51) Int. Cl.
 *A61K 38/26* (2006.01)
 *C12N 15/16* (2006.01)
 *A61K 38/00* (2006.01)

(52) U.S. Cl. ............. 435/440; 435/91.4; 435/91.41; 435/285.1; 435/70.1; 530/308; 530/344

(58) Field of Classification Search ............. 536/23.1; 435/69.1, 320.1, 440
See application file for complete search history.

(56) References Cited

U.S. PATENT DOCUMENTS

| 5,432,261 | A | 7/1995 | Kurono |
| 5,459,049 | A | 10/1995 | Kurono |
| 5,512,459 | A | 4/1996 | Wagner et al. |
| 5,545,618 | A | 8/1996 | Buckley et al. |
| 5,994,127 | A * | 11/1999 | Selden et al. ............ 435/325 |
| 6,037,143 | A | 3/2000 | Wagner et al. |
| 6,316,224 | B1 * | 11/2001 | Xia ........................ 435/69.1 |
| 6,403,361 | B1 | 6/2002 | Wagner et al. |

| 2002/0081735 | A1 * | 6/2002 | Xia ............................ 435/455 |

FOREIGN PATENT DOCUMENTS

| JP | 03-080096 | 4/1991 |
| JP | 06-306100 | 11/1994 |
| JP | 11-178574 | 7/1999 |
| WO | WO 95/17510 A1 | 6/1995 |
| WO | WO 9517510 A1 * | 6/1995 |
| WO | WO 97/29180 A1 | 8/1997 |
| WO | 98/08873 A1 | 3/1998 |
| WO | 99/43341 A1 | 9/1999 |
| WO | 99/43705 A1 | 9/1999 |
| WO | WO 01/98331 A2 | 12/2001 |

OTHER PUBLICATIONS

Li et al. (2008) GLP-1 C-terminal structures affect its blood glucose lowering-function, J. Pept. Sci., vol. 14, No. 7, pp. 777-785.*
Hui, H, Glucagon-Like Peptide 1 Induces Differentiation of Islet Duodenal Homeobox-1- Positive Pancreatic Ductal Cells Into Insulin-Secreting Cells, Diabetes, Apr. 2001, pp. 785-796, vol. 50.
Nielsen, J, Regulation of B-Cell Mass by Hormones and Growth Factors, Diabetes, Feb. 2001, pp. 825-829, vol. 50. Supplement 1.
Rachman, J., Normalization of Insulin Responses to Glucose by Overnight Infusion of Glucagon-Like Peptide 1 (7-36) Amide in Patients with NIDDM, Diabetes, Nov. 1996, pp. 1524-1530, vol. 45.
Tourrel, C., Persistent Improvement of Type 2 Diabetes in the Goto-Kakizaki Rat Model by Expansion of the B-Cell Mass During the Prediabetic Period With Glucagon-Like Peptide-1 or Exendin-4, Diabetes, May 2002, pp. 1443-1452, vol. 51.
Supplementary European Search Report for European Patent Application No. EP 02 75 2955, dated Jun. 15, 2005, 3 pages.

* cited by examiner

*Primary Examiner*—Jon P Weber
*Assistant Examiner*—Samuel W. Liu
(74) *Attorney, Agent, or Firm*—Perkins Coie LLP; Zhaohui Wang

(57) ABSTRACT

The present invention discloses a method of producing polypeptides, including insulinotropic GLP-1 (7-36) polypeptide and/or GLP-1 analogs, by ligating genes in a tandem way. Also disclosed are the recombinant polypeptides produced by such a method. Using the method of this invention, 1 to 32 copies of GLP-1 (7-36) and/or GLP-1 analog genes may be expressed in tandem and the desired polypeptide can be obtained after cleavage of a fusion protein and further processes of separation and purification thus making possible the production of recombinant polypeptides, including recombinant GLP-1 (7-36) and/or GLP-1 analogs on a large scale, at a significantly reduced production cost.

15 Claims, 8 Drawing Sheets

| AA | umol/ml | standard1 | standard2 | | | Theoretical Value umol/ml | Theoretical Value | | Observed Value |
|---|---|---|---|---|---|---|---|---|---|
| ASP | 1.262 | 494880 | 550385 | 0.66262 | 397190 | 371001 | 336258 | 0.69172 | 1 ASP | 1 |
| GLU | 1.53 | 484979 | 540078 | 0.80761 | 1284589 | 1204720 | 1046211 | 2.20035 | 4 GLU | 4 |
| SER | 2.5 | 706508 | 794452 | 1.327028 | 894195 | 838720 | 762088 | 1.54590 | 3 SER | 3 |
| GLY | 2.5 | 925846 | 1031086 | 1.730712 | 1090537 | 1017152 | 922763 | 1.43950 | 3 GLY | 3 |
| HIS | 2.5 | 839927 | 947554 | 1.580177 | 390603 | 358831 | 328458 | 0.56076 | 1 HIS | 1 |
| ARG | 2.5 | 776946 | 872754 | 1.458581 | 383719 | 357847 | 326426 | 0.60204 | 1 ARG | 1 |
| THR | 2.5 | 723374 | 810840 | 1.356657 | 620565 | 573989 | 537854 | 1.050059 | 2 THR | 2 |
| ALA | 2.5 | 795635 | 897032 | 1.496389 | 1431080 | 1338788 | 1152112 | 2.15194 | 4 ALA | 4 |
| PRO | 2.5 | 973169 | 1091622 | 1.825669 | | | | 0.00000 | 0 PRO | |
| TYR | 2.5 | 998194 | 1133800 | 1.884311 | 393160 | 369631 | 330419 | 0.47685 | 1 TYR | 1 |
| VAL | 2.5 | 976327 | 1105508 | 1.840169 | 787414 | 722761 | 644498 | 0.96047 | 2 VAL | 2 |
| Met | 2.5 | 942806 | 1067211 | 1.776706 | | | | 0.00000 | 0 Met | |
| CYS | 2.5 | 420909 | 478853 | 0.795191 | | | | 0.00000 | 0 CYS | |
| ILE | 2.5 | 996621 | 1130700 | 1.880253 | 404321 | 378597 | 336607 | 0.48928 | 1 ILE | 1 |
| LEU | 2.5 | 975516 | 1108565 | 1.841936 | 862110 | 789104 | 781561 | 1.08793 | 2 LEU | 2 |
| NLE | | 528511 | 603107 | 1 | 1068186 | 1036300 | 934742 | 0.00000 | 0 NLE | |
| PHE | 2.5 | 1005362 | 1147354 | 1.90233 | 776275 | 729651 | 637449 | 0.92552 | 2 PHE | 2 |
| LYS | 2.5 | 1870193 | 2134643 | 3.539009 | 1451777 | 1354803 | 1239821 | 0.94019 | 2 LYS | 2 |

Figure 7

METHOD OF PRODUCING INSULINOTROPIC GLP-1 (7-36) POLYPEPTIDE AND/OR GLP-1 ANALOGS

CROSS-REFERENCE TO RELATED APPLICATIONS

This is a continuation-in-part of PCT/CN02/00502 which bears an international filing date of 17 Jul. 2002, and which claims the priority to Chinese Patent Application Serial No. 01126278.8 filed 19 Jul. 2001.

FIELD OF THE INVENTION

This invention discloses a method of producing glucagon like peptide GLP-1 (7-36) polypeptide or glucagon like peptide-1 analogs by ligating genes in tandem. Also disclosed are the recombinant polypeptides produced by this method. Exogenous administration of GLP-1 (7-36) or GLP-1 analogs can stimulate the secretion of insulin.

BACKGROUND OF THE INVENTION

GLP-1 (glucagon like peptide-1) is a peptide hormone secreted by human intestinal cells, which forms from proteolytic cleavage of proglucagon by an L-cell-produced protease, and is therefore named glucagon like peptide-1. Multiple studies have shown that exogenous administration of GLP-1 enhances the effects of insulin secretion. For example, when blood glucose is over 6 mmol/L, a very low concentration of GLP-1 can play a significant role in increasing insulin secretion. Once the blood glucose is restored to a normal level, the further addition of GLP-1 shall no longer have any effect on insulin secretion.

GLP-1 is present as two forms in the human body, one is GLP-1 (7-36)-$NH_2$ (SEQ ID NO:2) which comprises of 30 amino acid residues with its C-terminal amidated. The other is GLP-1 (7-37) (SEQ ID NO:3) which comprises of 31 amino acid residues. Both GLP-1 (7-36)-$NH_2$ and GLP-1 (7-37) may have strong enhancing effects on insulin secretion.

Previous studies have shown that GLP-1 has more advantages than insulin in the treatment of type II diabetes mellitus. GLP-1 may: 1) increase the regulation of the transcription and translation of proinsulin gene, 2) enhance the secretion of insulin and C-peptide, 3) enhance the sensitivity of cellular insulin receptor, and 4) increase the total amount of β-cells. Moreover, GLP-1 may also lower or decrease: 1) the resistance to insulin and 2) the quantity of glycohemoglobin (HbA1c), fructosamine, glucagon and fatty acids. (Nielsen J. H., et al., Regulation of beta-cell mass by hormones and growth factors, *Diabetes*, 50, suppl., 1:S25-9, 2001; Hui H., et al., Glucagon-like peptide 1 induces differentiation of islet duodenal homeobox-1-positive pancreatic ductal cells into insulin-secreting cells, *Diabetes*, 50(4):785-96, 2001).

More notably, GLP-1 is observed to be capable of enhancing β-cell division and therefore increasing the total amount of β-cells, which has not been found in any other medicines used for diabetes treatment up until now. In addition, GLP-1 is effective in those patients who have failed to respond to treatment with sulfonylurea. Furthermore, administration of GLP-1 doesn't enhance insulin secretion when the concentration of blood glucose is restored to a normal level. Thus it doesn't result in hypoglycemia. For all of the abovementioned reasons, GLP-1 is regarded as a desirable medicine to treat diabetes mellitus. This is also verified by substantial clinical studies. (Rachman J., et al., Normalization of insulin response to glucose by overnight infusion of glucagon-like peptide 1(7-36) amide in patients with NIDDM, *Diabetes*, 45(11):1524-30, 1996; Doyle M. E., et al., Glucagon-like peptide-1, Recent Progress in Hormone Research, 56:377-99, 2001; Daniel J. Drucker, Minireview: The Glucagon-Like Peptides, *Endocrinology*, 142(2):521-527, 2001).

However, the cost of the chemical synthesis of GLP-1 is quite high. The retail price for reagent-grade GLP-1 is $400/mg, which greatly restricts its application in clinics. Some researchers have attempted to use genetic engineering methods to produce the recombinant GLP-1 either as a fusion protein or as a secreted protein. Yet the yield and the cost of this approach to produce GLP-1 have been far from satisfactory, thereby making large-scale production of GLP-1 at a low cost impossible at this stage.

This invention aims to develop a novel method of producing GLP-1 (7-36) and/or GLP-1 analogs by ligating genes in a tandem way. The method of the present invention can be used to simplify the process, to lower the production cost, and thereby making it possible to produce GLP-1 (7-36) and/or GLP-1 analogs on a large scale.

BRIEF SUMMARY OF THE INVENTION

This invention relates to a method of producing insulinotropic GLP-1 (7-36) polypeptide and/or GLP-1 analogs comprising:
(a) introducing two individual restrictive endonuclease cleavage sites capable of forming a hybrid site to the two terminals of the gene which may encode the GLP-1 (7-36) polypeptide or GLP-1 analogs;
(b) ligating the cohesive ends to form a hybrid site after digestion with restrictive endonucleases, and cloning into a vector N copies of the series-linked GLP-1 (7-36) gene, GLP-1 analogs gene, or interactively linked genes encoding GLP-1 (7-36) polypeptide or GLP-1 analogs, wherein N is an integer from 1 to 32;
(c) transforming the vector containing the series-linked gene into a host cell.
(d) expressing into the host cell a fusion protein containing N copies of a polypeptide wherein N is an integer from 1 to 32, the said fusion protein containing the GLP-1 (7-36) polypeptide, GLP-1 analogs or the combination thereof, but without any carrier protein;
(e) cleaving the fusion protein; and
(f) separating and purifying the GLP-1 (7-36) polypeptides and/or GLP-1 analogs.

The abovementioned two restrictive endonucleases capable of forming hybrids may include, but are not limited to, Bgl II and BamH I, Sal I and Xho I.

The vector in the method according to the present invention may contain N series-linked or interactively linked GLP-1 (7-36) genes and/or GLP-1 analog genes, wherein N is an integer from 1 to 32. Preferably, N is an integer from 8 to 32. More preferably, N should be 16 or 32.

The host cells used in the method according to the present invention may express a fusion protein containing N copies of GLP-1 (7-36) polypeptide and/or GLP-1 analogs, in which N is an integer from 1 to 32. The fusion protein may contain N copies of GLP-1 (7-36) polypeptide or GLP-1 analogs. Also it may contain multiple copies of both GLP-1 (7-36) polypeptide and GLP-1 analogs with the total copy numbers equal to N. In one embodiment, N is an integer from 8 to 32. In another embodiment, N is an integer from 16 or 32. Preferably, the host cells of this invention that express GLP-1 (7-36) and/or GLP-1 analogs are prokaryotic cells.

One embodiment of the present invention includes a method of producing GLP-1 (7-36) polypeptide and/or GLP-1 analogs, either by expressing a single copy of the polypeptide in an expression vector or, alternatively, by expressing a fusion protein containing multiple copies of the polypeptide and then cleaving this fusion protein into individual copies of the GLP-1 (7-36) and/or GLP-1 analogs sequence using the appropriate cleavage reagent. Cleavage reagents include, but are not limited to, cyanogen bromide, alkaline proteases such as trypsin, and enterokinase.

This invention also relates to the polypeptides of GLP-1 (7-36) and/or GLP-1 analogs produced by the method of this invention.

The GLP-1 (7-36) peptide produced by the method of this invention has the amino acid sequence as shown in Formula I (SEQ ID NO:1).

embodiment, the encoded fusion protein consists of 2-32 tandem copies of which each copy has an additional N-terminal Arg prior to the $His^7$ of the GLP-1 (7-36) or analog sequence and one or more additional amino acids following the C-terminal $Arg^{36}$ of the GLP-1 (7-36) or analog sequence. In one embodiment, the N-terminal Arg of the fusion protein sequence is preceded by a Met for purposes of beginning translation of the fusion protein. In an alternate embodiment, each copy of the insulinotropic polypeptide is preceded by a Met in addition to the N-terminal Arg of each copy.

In one embodiment of this method, the fusion protein is cleaved by treatment with a compound selected from the group consisting of: cyanogen bromide, alkaline proteases, enterokinases, endopeptidases, and combinations thereof. In one embodiment the alkaline protease is trypsin and internal lysine groups are acetylated prior to trypsin treatment. The

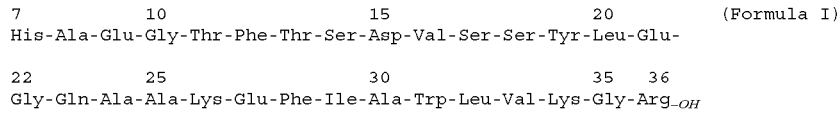

```
7          10              15                  20           (Formula I)
His-Ala-Glu-Gly-Thr-Phe-Thr-Ser-Asp-Val-Ser-Ser-Tyr-Leu-Glu- 22          25              30              35   36
Gly-Gln-Ala-Ala-Lys-Glu-Phe-Ile-Ala-Trp-Leu-Val-Lys-Gly-Arg_OH
```

In one embodiment of the invention a method is provided for producing an expression vector comprising multiple tandem copies of a gene encoding a desired polypeptide by constructing a vector comprising the gene and four individual restriction enzyme sites A-D in a relative order A-C-gene-B-D, wherein restriction enzyme sites C and B are capable of forming a hybrid site lacking restriction enzyme sites C and B. An aliquot of the resultant vector is digested with endonucleases C and D and a resulting double digested gene fragment is isolated. A second aliquot of the vector is digested with endonucleases B and D and a resulting double digested vector including the gene is isolated. Ligation of the double digested gene fragment and the double digested vector comprising the gene, forms a vector including N tandem copies of the gene linked by the hybrid site lacking restriction enzyme sites C and B. By repeating the above steps, beginning each time with a vector product of the prior series of steps, a vector product is obtained having N tandem copies of the gene which double with each series. In one embodiment, N is an integer from 2-32.

In one embodiment of the invention, restriction endonucleases sites C and B capable of forming a hybrid site are Bgl II and BamH I. In an alternative embodiment, restriction endonucleases sites C and B capable of forming a hybrid site are Sal I and Xhol I.

In one embodiment of the invention, the gene encoding a desired polypeptide is designed to encode one or more additional N-terminal amino acids selected from the group consisting of: Met; Arg; Met-Arg; Met-Met-Arg; Asp-Asp-Asp-Asp-Lys (SEQ ID NO:31); and combinations thereof.

In one embodiment of the invention, the polypeptide is insulinotropic, including polypeptides selected from the group: GLP-1 (7-36); GLP-1 analogs; and exendin-4 analogs. In one embodiment, the polypeptide is GLP (7-36) and N is an integer from 8 to 32.

In one embodiment of the invention, a method of producing an insulinotropic polypeptide is provided in which a host cell expresses from a vector an encoded fusion protein comprising 2-32 tandem copies of the insulinotropic polypeptide, wherein each copy comprises a cleavable N-terminal Arg or cleavable spacer. The fusion protein is isolated and cleaved at the cleavable N-terminal Arg or cleavable spacer. The insulinotropic polypeptide is then separated and purified. In one internal lysine groups may be acetylated by treatment with an anhydride followed by deprotection after trypsin treatment. Suitable anhydrides include: acetic anhydride; maleic anhydride; citraconic anhydride, and 3, 4, 5, 6-tetrahydrophthalic anhydride.

In one embodiment of the method, the insulinotropic polypeptide is selected from the group consisting of: GLP-1 (7-36) (SEQ ID NO:1), GLP-1 (7-36)-$NH_2$ (SEQ ID NO:2), $Gly^8$-GLP-1 (7-36) (SEQ ID NO:4), $Val^8$-GLP-1 (7-36) (SEQ ID NO:5), $Asp^{11}$-GLP-1 (7-36) (SEQ ID NO:6), $Ala^{16}$-GLP-1 (7-36) (SEQ ID NO:7), $Glu^{22}$-GLP-1 (7-36) (SEQ ID NO:8), $His^{23}$-GLP-1 (7-36) (SEQ ID NO:9), $Glu^{24}$-GLP-1 (7-36) (SEQ ID NO:10), $Trp^{26}$-GLP-1 (7-36) (SEQ ID NO:11), $Ala^{27}$-GLP-1 (7-36) (SEQ ID NO:12), $Glu^{30}$-GLP-1 (7-36) (SEQ ID NO:13, $Asp^{33}$-GLP-1 (7-36) (SEQ ID NO:14), $Glu^{34}$-GLP-1 (7-36) (SEQ ID NO:15), $Thr^{35}$-GLP-1 (7-36) (SEQ ID NO:16), $Gly^8$-$Glu^{24}$-GLP-1 (7-36) (SEQ ID NO:17), $Leu^8$-$Ala^{33}$-GLP-1 (7-36) (SEQ ID NO:18), and exendin-4 analogs.

In one embodiment the insulinotropic polypeptide is GLP-1 (7-36) (SEQ ID NO 1) and the cleavage spacer is an N-terminal Arg. The GLP-1 copy optionally be preceded by an N-terminal Met-Arg and the isolated fusion protein treated with cyanogen bromide followed by cleavage with clostripain protease to generate monomeric GLP-1 (7-36).

BRIEF DESCRIPTION OF THE DRAWINGS

FIG. 7 shows the amino acid analysis results of the recombinant GLP-1 (7-36) polypeptide.

DETAILED DESCRIPTION OF THE INVENTION

Figure 1:
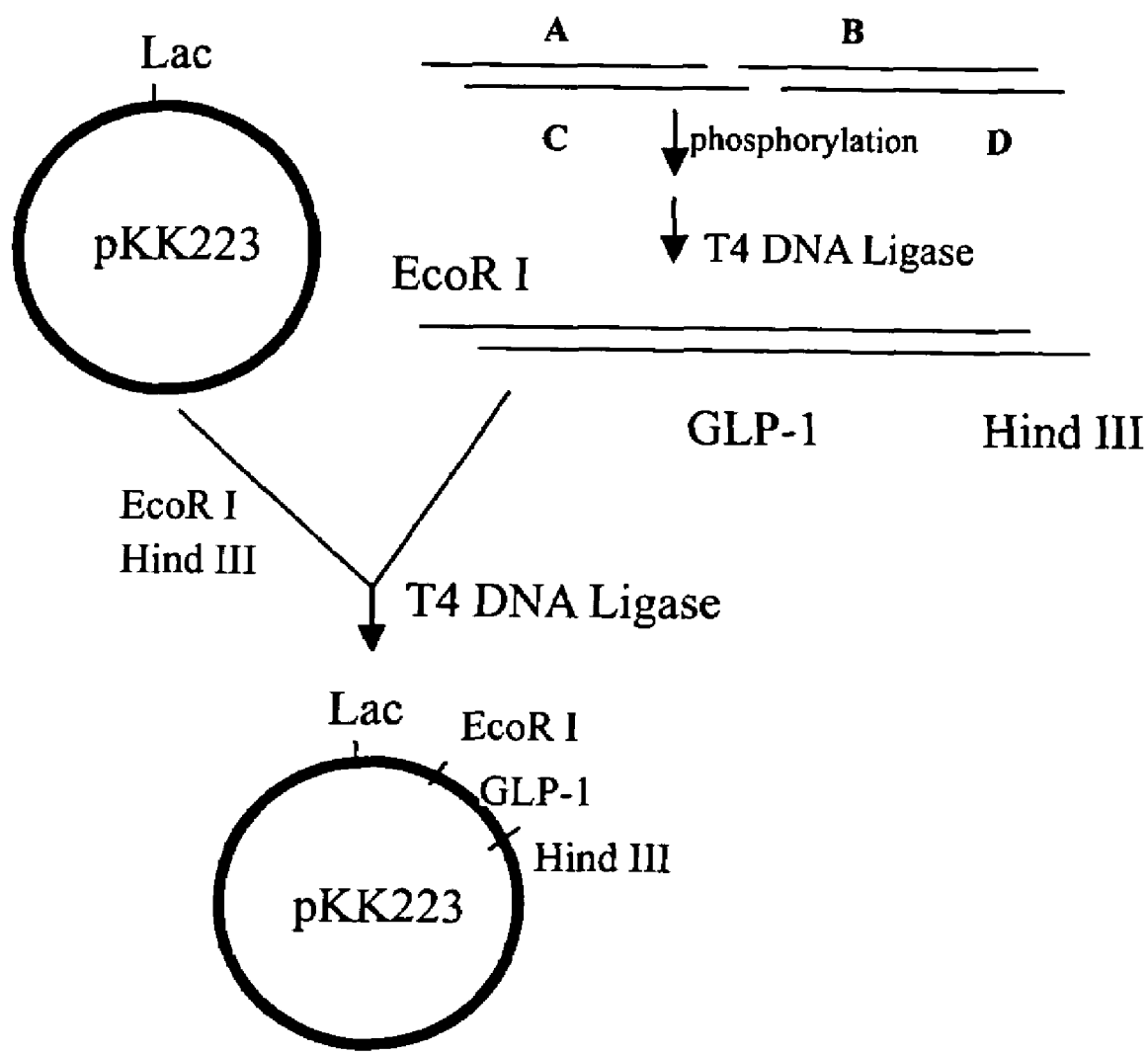
FIG. 1 depicts the process to construct a expression vector containing one copy of the gene encoding GLP-1 (7-36) polypeptide.

The present invention provides a method, which could present a hybrid sites to ligate multiple copies of genes encoding GLP-1 (7-36) or GLP-1 analogs in tandem. Expression of the resulting series-linked or interactively linked DNA fragments may yield a fusion protein containing multiple copies of GLP-1 (7-36) and/or GLP-1 analogs. After cleavage of the fusion protein and further purification, large quantities of GLP-1 (7-36) and/or GLP-1 analogs may then be obtained. The method of the present invention encompasses both method directed to single copies of the genes for these peptides, and preferably, to multiple copies of these genes that are tandemly linked so as to produce fusion proteins which are then cleaved to produce multiple copies of the desired peptide.

In the latter case, one embodiment of the present invention is specifically directed to the alteration of the sequences of these peptides to allow for the cleavage of the multimeric fusion proteins produced by these methods by trypsin, which normally is specific for either Arg or Lys residues. In one method of the invention, Arg is preferably added to the N- or C-terminus of each gene, and any Arg residues internal to these genes are removed or more preferably substituted by recombinant methods. In these methods it may also be necessary to remove internal Lys residues, which are also cleaved by trypsin, or to protect such residues from trypsin cleavage. One specific method of protection contemplated herein is the acetylation of internal Lys residues to prevent their cleavage by trypsin.

GLP-1 (7-36) of this invention has the amino acid sequence as shown in Formula I, with the C-terminal amidated form GLP-1 (7-36)-$_{NH2}$. "GLP-1 analogs" (synonymously, "derivatives") as used herein refer to those polypeptides which may be obtained by alteration, substitution or modification of one or more amino acid residue(s) in the sequence as shown in Formula I, or in the amino acid sequence of the naturally occurring GLP-1 (7-37)$_{OH}$ polypeptide. In the present invention, "protein," "peptide," and "polypeptide" are used synonymously.

Previous studies have shown that many GLP-1 analogs have similar characteristics in enhancing the secretion of insulin. Representatives of GLP-1 analogs include those described in U.S. Pat. No. 5,545,618 and WO 01/98331 A2.

Representatives of GLP-1 analogs may include, but are not limited to, $Gly^8$-GLP-1 (7-36) (SEQ ID NO:4), $Val^8$-GLP-1 (7-36) (SEQ ID NO:5), $Asp^{11}$-GLP-1 (7-36) (SEQ ID NO:6), $Ala^{16}$-GLP-1 (7-36) (SEQ ID NO:7), $Glu^{22}$-GLP-1 (7-36) (SEQ ID NO:8), $His^{23}$-GLP-1 (7-36) (SEQ ID NO:9), $Glu^{24}$-GLP-1 (7-36) (SEQ ID NO:10), $Trp^{26}$-GLP-1 (7-36) (SEQ ID NO:11), $Ala^{27}$-GLP-1 (7-36) (SEQ ID NO:12), $Glu^{30}$-GLP-1 (7-36) (SEQ ID NO:13, $Asp^{33}$-GLP-1 (7-36) (SEQ ID NO:14), $Glu^{34}$-GLP-1 (7-36) (SEQ ID NO:15), $Thr^{35}$-GLP-1 (7-36) (SEQ ID NO:16), $Gly^8$-$Glu^{24}$-GLP-1 (7-36) (SEQ ID NO:17), $Leu^8$-$Ala^{33}$-GLP-1 (7-36) (SEQ ID NO:18), In this nomenclature a changed amino acid in the peptide sequence is indicated by giving the name of the new amino acid with the position of the change relative to the wild-type GLP-1 sequence indicated as a superscript. Thus $Gly^8$-GLP-1 (7-36) refers to the GLP-1 (7-36) sequence where the Ala residue at GLP-1 position 8 (i.e., at GLP-1 (7-36) position 2) has been changed to a Gly residue.

Preferably, GLP-1 analogs of the present invention may contain amino acid residue(s) of conservative substitution. More preferably, these GLP-1 analogs may contain amino acid residue(s) of highly conservative substitution.

As used herein, a "conservative substitution" is the replacement of an amino acid that has the same net electronic charge and approximately the same size and shape.

A "highly conservative substitution" is the replacement of an amino acid with another amino acid that has the same functional group in the side chain and nearly the same size and shape. For example, amino acids with aliphatic or substituted aliphatic amino acid side chains have nearly the same size when the total number of carbon and heteroatoms in their side chains differ by no more than two. They have nearly the same shape when they have the same number of branches in their side chains. Examples of highly conservative substitution include valine for leucine, threonine for serine, aspartic acid for glutamic acid and phenylglycine for phenylalanine. Examples of substitutions which are not highly conservative include alanine for valine, alanine for serine and aspartic acid for serine.

Therefore, the present invention provides a method of producing insulinotropic GLP-1 (7-36) polypeptide and/or GLP-1 analogs comprising of:

(a) introducing two individual restriction endonuclease cleavage sites capable of forming a hybrid site to the two terminals of the gene which may encode the GLP-1 (7-36) polypeptide or GLP-1 analogs;

(b) ligating the cohesive ends to form a hybrid site after digestion with restriction endonucleases, and cloning into a vector N copies of the series-linked GLP-1 (7-36) gene, GLP-1 analogs gene, or interactively linked genes encoding GLP-1 (7-36) polypeptide or GLP-1 analogs, wherein N is an integer from 1 to 32;

(c) transforming the vector containing the series-linked gene into a host cell.

(d) expressing into the host cell a fusion protein containing N copies of a polypeptide wherein N is an integer from 1 to 32, the said fusion protein containing the GLP-1 (7-36) polypeptide, GLP-1 analogs or the combination thereof, but without any carrier protein;

(e) cleaving the fusion protein; and (f) separating and purifying the GLP-1 (7-36) polypeptides and/or GLP-1 analogs.

In the present invention, "insulinotropic" peptides are peptides with GLP-1-like insulinotropic activity, i.e., peptides that stimulate, or cause the stimulation of, the synthesis or expression of the hormone insulin. Assays for such activity are well known to the skilled artisan. Insulinotropic peptides contemplated herein include GLP-1 (7-36), exendin-4, and analogs and derivatives thereof, including the specific analogs and derivatives disclosed elsewhere herein. As intended herein, "derivatives," "analogs," and "variants" are used synonymously.

In such tandemly linked exendin-4 or exendin-4 derivative constructs, "tandemly linked" or "tandem linkage" as it refers to the peptides of the invention is used to indicate any linkage between the peptides of interest that allows for the production of a single fusion protein that may be cleaved by the appropriate cleavage reagent to produce separate peptides of the desired sequence. As described below in the discussion of GLP-1 fusion peptides, such cleavage reagents include, e.g., cyanogen bromide ("CNBr"), alkaline proteases such as trypsin, and enterokinase.

In the present invention "tandemly linked" or "tandem linkage" is also used to refer to the joining of DNA sequences of the invention. In this context, "tandemly linked" DNA sequences are DNA sequences that are so joined that they serve as the template for the production by transcription/translation of a tandemly linked fusion peptide.

The two restrictive endonuclease which can be used to form a "hybrid site" may include, but is not limited to, Bgl II and BamH I, Sal I and Xho I. For example, the base sequence recognized by Bgl II is A|GA TCT, while the one recognized by BamH I is G|GA TCC. After digesting the two sequences with corresponding restriction enzymes, ligation of the resulting complementary cohesive ends may form a sequence of AGA TCC or GGA TCT, which cannot be dissected by either Bgl II or BamH I. Such a sequence is called a "hybrid site" which may be used to ligate multiple copies of certain genes in tandem.

The fusion proteins of the present invention relating to GLP-1 are composed of multiple copies of GLP-1 (7-36) and/or GLP-1 analogs that are tandemly linked. As contemplated herein, "tandem linkage" as it applies to the GLP-1 (7-36) and GLP-1 analogs of the invention includes any linkage between the peptides of interest that allows for the production of a single fusion protein that may be cleaved by the appropriate reagent to produce separate peptides of the desired sequence.

Thus in one aspect of the present invention, two or more copies of GLP-1 (7-36) may be joined to one another without any intervening amino acid sequence, e.g., with the C-terminal Arg of the first GLP-1 (7-36) sequence immediately followed by the N-terminal His residue of the next GLP-1 (7-36) sequence. DNA methods for producing such constructs are well known in the art, and include the use of PCR methods or chemical synthesis methods to produce tandem copies of a gene sequence encoding the GLP-1 (7-36) peptide with no intervening codons between these sequences. In this example, trypsin may be used to cleave the resulting fusion protein after the C-terminal Arg to produce GLP-1 (7-36) peptides with the wild-type N- and C-termini. This method is also contemplated for use with GLP-1 analogs, where such analogs preserve the wild-type N- and C-termini of the GLP-1 (7-36) sequence.

In another aspect of the present invention, between the two tandemly linked peptides (two GLP-1 (7-36) polypeptides, two GLP-1 analog polypeptides, or one GLP-1 (7-36)), the amino acid sequence, Xaa . . . Xaa, of one or more amino acid residues connected to each other, together separate the tandemly linked peptides. This spacer amino acid sequence is encoded by a spacer DNA sequence separating GLP-1 (7-36) and/or GLP-1 analog DNA sequence. As contemplated herein, the spacer DNA sequence is constructed so as to encode a series of one or more amino acids in frame with both the upstream and downstream GLP-1 (7-36) and/or GLP-1 analog sequences, thereby ensuring that a continuous fusion protein is produced.

For the purpose of cleavage, the peptide bond formed between the N-terminal or C-terminal end of each desired polypeptide (GLP-1 (7-36) or GLP-1 analog) and the above-mentioned Xaa . . . Xaa spacer amino acid sequence residue or residues must be a specifically cleavable peptide bond. Thus a "specifically cleavable peptide bond" as used herein refers to a peptide bond that can be specifically recognized and cleaved by certain chemical reagents or proteases. As a result of cleavage, the peptide chain is ruptured. The amino acid residues used to form a specifically cleavable peptide bond with the N-terminus of GLP-1 (7-36) or a GLP-1 analog are called bond-forming amino acids ("BFAA"). BFAA may include, but are not limited to: Met, which may be recognized by CNBr; Arg, which may be recognized by alkaline protease; and, the amino acid sequence of Asp-Asp-Asp-Asp-Lys (SEQ ID 31), which may be recognized by enterokinase.

A fusion protein may be cleaved at a specifically cleavable peptide bond by any method capable of such cleavage. In one such cleavage process, the fusion protein is broken into multiple molecules of GLP-1 (7-36) and/or GLP-1 analog polypeptide, with each polypeptide having several amino acid(s) attached to its C-terminal end but with the N-terminal end corresponding to the native N-terminus. This process is referred to herein as N-terminal cleavage of the target peptide.

For a fusion protein comprising multiple copies of GLP-1 (7-36) separated by a spacer amino acid sequence Xaa . . . Xaa, for example, the N-terminal cleavage of this fusion protein may be used to generate multiple copies of GLP-1 (7-36)-Xaa . . . Xaa. Since the native amino acid residue at the C-terminal end of GLP-1 (7-36) is Arg, using proteases which specifically recognize the peptide bond formed at the carboxyl of Arg to cleave the multiple copies of GLP-1 (7-36)-Xaa . . . Xaa will result in multiple molecules of GLP-1 (7-36) polypeptide.

The complementary process occurring at the C-terminus of the target peptide is referred to herein as C-terminal cleavage. C-terminal cleavage of a GLP-1 (7-36) fusion protein at the terminal Arg residue of the GLP-1 (7-36) sequence, for example, will produce the GLP-1 (7-36) sequence preceded by the Xaa . . . Xaa spacer amino acid sequence, i.e., the sequence Xaa . . . Xaa-GLP-1 (7-36). As contemplated in the present invention, the order for the N-terminal cleavage process and the C-terminal cleavage process can be exchanged.

Typically, an Arg residue is added to the N-terminus of GLP-1 (7-36), and the appropriate protease is used for cleavage, i.e., a protease which specifically recognizes the peptide bond formed at the carboxyl of Arg. In this procedure, the fusion protein is cut into multiple molecules of GLP-1 (7-36) polypeptide without other attached residues, since the amino acid residue at the C-terminal amino acid of GLP-1 (7-36) is Arg. It is also feasible to add Met to the N-terminus of GLP-1 (7-36). In this embodiment of the present invention, the peptide bond formed with this Met can be cleaved by CNBr, and the resulting peptide is then cleaved by the appropriate protease to yield multiple molecules of GLP-1 (7-36), i.e., by an Arg-specific protease, since the C-terminal amino acid of GLP-1 (7-36) is Arg. The present invention also contemplates a situation in which the order for the N-terminal cleavage and the C-terminal cleavage is exchanged.

It is also possible to add the amino acid sequence of Asp-Asp-Asp-Asp-Lys (SEQ ID NO:31) to the N-terminal end of GLP-1 (7-36), where this sequence can be specifically cleaved by the protease enterokinase. In this situation, proteolytic cleavage by enterokinase will yield multiple molecules of GLP-1 (7-36) peptide. It is preferable to use Arg addition to the N-terminus of GLP-1 (7-36) and GLP-1 analogs.

Based on the amino acid sequence of GLP-1 (7-36) or GLP-1 analogs, the gene encoding GLP-1 (7-36) or GLP-1 analogs can be synthesized with the addition of a codon encoding a "peptide forming amino acid" at the 5' terminal end of the synthetic fragment. A linkage sequence and the sequence recognized by restriction enzyme are also included at the two ends of the synthetic gene. After modification, a DNA fragment can be formed which contains the codon encoding GLP-1 (7-36) or GLP-1 analogs and the base pairs at the two ends that are recognized by restriction endonucleases. This fragment can be used to link multiple copies of GLP-1 (7-36) or GLP-1 analog in tandem and is then called a "gene for series-connection."

It is also possible to modify the DNA sequence of naturally occurring GLP-1 to generate a "gene for series-connection." It is preferable to use synthetic methods to prepare the gene in the present invention.

It is well known that one amino acid may be encoded by multiple codons. Thus a GLP-1 or exendin-4 DNA sequence, or GLP-1 or exendin-4 derivative DNA sequence, as used herein, refers to any DNA sequence that encodes a specified GLP-1 or exendin-4 peptide sequence, or GLP-1 or exendin-4 derivative peptide sequence. One skilled in the art can deduce and synthesize various DNA sequences and sequence combinations encoding GLP-1 (7-36) or GLP-1 analogs. In the present invention, codons with high frequency in *E. coli* are preferred.

The genes encoding GLP-1 (7-36) or GLP-1 analog peptides can be generated in several ways, including ligating several synthetic fragments by cohesive ends or blunt ends to generate the target gene, or by synthesizing the whole target gene by chemical synthesis. It is preferable to synthesize several fragments and then generate the target gene by ligation.

The restriction endonuclease cleavage sites that can form hybrid sites to the 5' and 3' ends of the genes encoding GLP-1 (7-36) or GLP-1 analogs for the purpose of linking multiple copies of gene in tandem require careful selection and construct design. The selection of recognition sites of restriction endonucleases for the purpose of cloning is based on the endonuclease sites in a vector.

A preferred embodiment of this invention is directed to the use of codons with high frequency in *E. coli* to synthesize four gene fragments. After ligation, the resulting recombinant GLP-1 (7-36) gene has restriction endonucleases sites of Bgl II and BamHI at its two ends. These sites are used to link these genes in tandem. The cloning sites of EcoRI and Hind III are used for insertion into a vector. The positions for the Bgl II and BamHI recognition sites may be exchanged.

In another preferred embodiment of the present invention, codons with high frequency in *E. coli* are used to synthesize four gene fragments. After ligation, the resulted GLP-1 (7-36) gene has restriction endonuclease sites of SalI and XholI which are used for linking the genes in tandem. The cloning sites of EcoRI and Hind III are used for insertion into a vector.

Multiple copies of genes encoding GLP-1 (7-36) or GLP-1 analogs can be linked in tandem by using the above-mentioned endonuclease sites, and then can be cloned into a vector. These genes linked in tandem can also be mixed-and-matched. The term "mix-and-match" refers to any number of DNA fragments encoding GLP-1 (7-36) and GLP-1 analogs that are linked together in tandem in any order. Vectors suitable for this purpose can be chromosome-derived, non-chromosome-derived, or synthetic DNA. These vectors may include, but are not limited to, phage DNA, bacillus virus, bacterial plasmid, yeast plasmid, and vectors derived from a combination of phage, plasmid and viral DNA. The viral DNA may include, but is not limited to, bovine and poultry smallpox virus, adenovirus, and pseudorabies virus. Many other suitable vectors are well known to one skilled in the art.

Any plasmid or vector that exist and replicates stably in host cells may be used in this invention.

Representative but non-limiting examples of the expression vectors contemplated in the present invention include those used in bacterial systems, such as commercially available plasmids pKK233-2, pKK223-3, pEZZ18, pUC18, pUC19, and pT7 (Amersham Pharmacia Biotech).

In the present invention the target gene is linked to an appropriate promoter on an expression vector. A promoter is a sequence that can regulate and control gene transcription, i.e., is capable of driving the expression of a protein sequence using a DNA template. The representative examples of promoter include lac, trp, tac of *E. coli*; T7 of phage; $P_L$ of $\lambda$ phage, and other known promoters existing in prokaryotic cells, eukaryotic cells, and viruses that control gene expression. Particularly preferred bacterial promoters include lac, lacZ, T3, T7, Protein A promoter, gpt, $\lambda P_R$, $P_L$ and trp. The selection of appropriate promoters is apparent to one skilled in the art.

In addition, the preferred expression vector may have one or more selection marker gene(s) in order to facilitate screening of the host cells. Such marker genes include tetracycline and penicillin resistance genes in *E. coli*, and dihydrofolate reductase and neomycin resistance genes in eukaryotic expression systems.

The expression vectors of the present invention may contain N copies of the genes linked in tandem, in which N is an integer from 1 to 32. Preferably, N is an integer from 8 to 32. More preferably, N is either 16 or 32. Thus in one embodiment of this invention, the expression vector contains 1 copy of GLP-1 (7-36). In another embodiment of this invention, the expression vector contains 2 copies of GLP-1 (7-36) linked in tandem. In another embodiment of example presented in this invention, the expression vector contains 4 copies of GLP-1 (7-36) linked in tandem. In another embodiment of this invention, the expression vector contains 8 copies of GLP-1 (7-36) linked in tandem. In another embodiment of this invention, the expression vector contains 12 copies of GLP-1 (7-36) linked in tandem. In preferred embodiment of this invention, the expression vector contains 16 copies of GLP-1 (7-36) linked in tandem. In another embodiment of example presented in this invention, the expression vector contains 32 copies of GLP-1 (7-36) linked in tandem.

The inventors have deposited a bacterial strain carrying the recombinant expression vector pKK223-3 which contains 32 copies of GLP-1 (7-36) gene linked in tandem. The deposit number of the strain is CGMCC No. 0599.

The vectors of the present invention carrying multiple copies of gene(s) and appropriate promoters or other gene expression regulatory components can be transformed into appropriate host cells to express the fusion proteins in the host cells. Therefore, this invention also relates to host cells that are capable of expressing GLP-1 (7-36) or GLP-1 analog polypeptides. The expression vector can be introduced into host cells by genetic engineering method such as transformation, transfection, or infection. For example, the expression vector may be introduced via transformation with calcium chloride, transfection in the presence of DEAE-dextran as a carrier, or by electroporation. These methods will efficiently transfer the vector containing multiple copies of gene(s) of the present invention into host cells. The vectors referred to herein can be plasmids, viral particles, or bacterial phages.

Suitable host cells may include, but are not limited to, bacterial cells such as *E. coli, streptococcus, salmonella,* and eukaryotic cells such as yeast. The selection of the appropriate host cells is apparent to one skilled in the art. For the purpose of lowering production cost, prokaryotic cells are the preferred host cells. Representative examples include a variety of strains of *E. coli*, e.g., JM103, JM109, HB101, DH5α, and C600.

The host cells of the present invention contain an expression vector containing N copies of a gene encoding GLP-1 (7-36) and/or GLP-1 analogs, in which N is an integer from 1 to 32. Correspondingly, the host cells express fusion proteins containing N copies of GLP-1 (7-36) and/or GLP-1 analogs linked in tandem, in which N is an integer from 1 to 32, preferably N is an integer from 8 to 32, and more preferably N is an integer from 16 to 32. The fusion protein does not contain any other carrier proteins.

In one embodiment of the present invention, the expression plasmid containing 1 copy of GLP-1 (7-36) gene is transformed into *E. coli* JM103 cells. The genetically engineered JM103 cells consequently contain one GLP-1 (7-36) gene. In another preferred embodiment, the expression plasmid containing 2 copies of GLP-1 (7-36) gene is transformed into *E. coli* JM103 cells. In this embodiment, the genetically engineered JM103 cells express a fusion protein containing two GLP-1 (7-36) polypeptides. In another embodiment, the expression plasmid containing 4 copies of GLP-1 (7-36) gene is transformed into *E. coli* JM103 cells. In this embodiment, the genetically engineered JM103 cells express a fusion protein containing 4 GLP-1 (7-36) polypeptides. In another embodiment of this invention, the expression plasmid containing 8 copies of GLP-1 (7-36) gene is transformed into *E. coli* JM103 cells. In this embodiment, the genetically engineered JM103 cells express a fusion protein containing 8 GLP-1 (7-36) polypeptides. In another embodiment of this invention, the expression plasmid containing 12 copies of GLP-1 (7-36) gene is transformed into *E. Coli* JM103 cells. In this embodiment, the genetically engineered JM103 cells express a fusion protein containing 12 GLP-1 (7-36) polypeptides. In still another embodiment of this invention, the expression plasmid containing 16 copies of GLP-1 (7-36) gene is transformed into *E. coli* JM103 cells. In this embodiment, the genetically engineered JM103 cells express a fusion protein containing 16 GLP-1 (7-36) polypeptides. In still another embodiment of this invention, the expression plasmid containing 32 copies of GLP-1 (7-36) gene is transformed into *E. coli* JM103 cells. In this embodiment, the genetically engineered JM103 cells express a fusion protein containing 32 GLP-1 (7-36) polypeptides.

In accordance with the Budapest Treaty on the International Recognition of the Deposit of Microorganisms for the Purposes of Patent Procedure, a genetically engineered bacterial strain which expresses the fusion protein containing 32 GLP-1 (7-36) polypeptides has been deposited with China General Microbiological Culture Collection Center (CGMCC). The deposit date is Jul. 11, 2001, the deposit Number is CGMCC No. 0599. The deposited strain carries a plasmid containing 32 serial-linked copies of GLP-1 (7-36) gene. The deposit was made merely as a convenience for those of skill in the art and is not an admission that a deposit is required under 35 U.S.C § 112. Any reproduction, usage or sale of the deposited microorganism needs particular permission from the inventors. Such permissions have not been granted herein.

The genetically engineered bacterial strains of the present invention are cultured under appropriate conditions to produce and accumulate fusion proteins composed of N copies of the linked polypeptides. The culturing conditions such as culturing media, temperature, humidity and pH value are apparent to one skilled in the art.

After the host cells have grown to a proper density, they can be harvested, e.g., by centrifugation. The harvested cells are then ruptured by physical or chemical methods, and the resulting product is collected and subject to further purification.

The microorganism cells expressing recombinant proteins can be ruptured by any conventional means, which may include, but are not limited to, freeze and thaw cycles, ultrasonic or mechanical treatment, or cellular lysis reagents. The selection of appropriate protocols to break up host cells is apparent to one skilled in the art.

The fusion proteins presented in the present invention are composed of multiple polypeptides. These polypeptides may be GLP-1 (7-36) or GLP-1 analogs or a mixture of these polypeptides. In one aspect of the invention, there are several amino acid residues between the two neighboring peptides. These two peptides can be two GLP-1 (7-36) peptides, two GLP-1 analog peptides, or one GLP-1 (7-36) and one GLP-1 analog. The amino acid residue(s) linked to the N-terminus of each GLP-1 (7-36) or GLP-1 analog are "peptide forming amino acids," as described above. Under suitable cleavage conditions and with proper substances, the fusion protein may be cleaved at the N-terminus of each GLP-1 (7-36) or GLP-1 analog peptide, thereby producing multiple GLP-1 (7-36) or GLP-1 analog peptides with several amino acids attached to its C-terminus. For example, the fusion protein composed of N copies of GLP-1 (7-36) polypeptide is cleaved to yield GLP-1 (7-36)-Xaa . . . Xaa, in which Xaa . . . Xaa represents one or more amino acid residue(s) in tandem. Further, since the C-terminus of GLP-1 (7-36) is an Arg residue, the peptide bond formed between the Arg and the Xaa . . . Xaa can be specifically cleaved by the appropriate protease to yield GLP-1 (7-36).

In order to simplify the cleavage process, Arg may be chosen as the bond forming amino acid, with a protease used that will specifically cleave the peptide bond formed through the carboxyl group of Arg. In this way, the fusion protein can be hydrolyzed into multiple molecules of the polypeptide by a single cleavage step.

In one embodiment of this invention, Met is chosen as the peptide forming amino acid. CNBr is used to break the peptide bond formed by the participation of the carboxyl group of Met, followed by a protease (for example, clostripain) which specifically recognizes the peptide bond formed by the participation of the carboxyl group of Arg. This process yields multiple GLP-1 (7-36) peptides with no C-terminal amidation modification. The present invention contemplates that the order of above-mentioned two steps of cleavage may be switched.

In another embodiment of the present invention, Arg is chosen as the peptide forming amino acid, with the protease trypsin used to specifically cleave the peptide bond formed by the participation of the carboxyl group of Arg. In this situation, it may be necessary to alter trypsin reaction conditions to prevent trypsin cleavage at internal Lys residues. For example, it may be necessary to use high pH conditions for trypsin cleavage, such as are disclosed in WO 95/17510.

Alternatively, various anhydrides may be used in this process to protect any internal Lys residue or residues from cleavage by trypsin. For example, although WO 95/17510 is directed only to the use of high pH conditions to prevent trypsin cleavage at the internal Lys residues of GLP-1 (7-36), the present invention specifically contemplates acetylation of the two internal Lys residues of GLP-1 (7-36) including by acetic anhydride, citraconic anhydride, or 3, 4, 5, 6-tetrahydrophthalic anhydride as a superior alternative for the protection of these residues from trypsin cleavage. As a result, trypsin can be used to specifically cleave the peptide bond formed by the participation of the carboxyl group of Arg without cleaving at any Lys residues. Therefore one step of cleavage can yield multiple GLP-1 (7-36) peptides where, furthermore, none of these GLP-1 (7-36) peptides has a C-terminal amidation modification.

In accordance with an embodiment with the method of the present invention, acetylation of the internal $Lys_{14}$ residue in exendin-4 or of the two internal Lys residues of GLP-1 (7-36) may be accomplished by acetylation of the $\epsilon$-$NH_2$ in the Lys residues. Such acetylation is conducted by, e.g., suspending the purified wet inclusion body in a $Na_2CO_3$ solution, and then gradually adding maleic anhydride derivatives to the solution with stirring at room temperature at pH 8. After 4 hours, the reaction mixture is dialyzed overnight in phosphate buffer, and the fusion protein in the dialyzed reaction mixture is digested with trypsin at a ratio of protein-to-trypsin of about 1000:0.5-2 (w/w) at 30° C. for 2 hours. During the reaction, digestion is monitored by HPLC analysis.

After digestion, the acyl group from the $\epsilon$-$NH_2$ is deprotected by acidifying the reaction mixture for 4-6 hours at room temperature using 4M HCl. Finally, the acidified reaction is neutralized with $NaHCO_3$ to pH 5.0, the precipitate is centrifuged, and the crude exendin-4 derivative is collected from the precipitate.

After fusion protein cleavage, highly purified polypeptide can be obtained via a series of separation and purification steps, e.g., by chromatographic methods. Such chromatographic methods may include, but are not limited to, ion-exchange, hydrophobic, size exclusion, and reverse phase chromatography. The media used in these methods may be purchased from commercial vendors, such as Armersham Pharmacia Biotech, Whatman, Merck KGaA, and Grace Vydac etc. Single chromatography or a combination of multiple chromatography steps may also be used in the purification processes. In general, HPLC is used as a means of purification. Typically, C18 reversed phase chromatography with a TFA-$CH_3CN$ system as mobile phase is utilized. These chromatographic methods are well known to one skilled in the art.

It should be pointed out that, although the method to produce GLP-1 (7-36) polypeptide has been described hereinafter to illustrate the present invention, it should be apparent to one skilled in the art based on the disclosure presented herein that such method can also be used to produce GLP-1 analogs, as long as the amino acid residue at the N-terminus and at the C-terminus of a GLP-1 analog can form a specifically cleavable peptide bond with the neighboring amino acid residue(s), while the cleavage will not occur internally within the polypeptide. Therefore, methods to produce GLP-1 analogs by ligating genes in tandem are within the scope of the present invention.

Typically, a GLP-1 analog will contain Arg at its C-terminus, but no Arg at any other position of the amino acid sequence of the analog. Such GLP-1 analogs may include, but are not limited to: $Gly^8$-GLP-1 (7-36) (SEQ ID NO:4), $Val^8$-GLP-1 (7-36) (SEQ ID NO:5), $Asp^{11}$-GLP-1 (7-36) (SEQ ID NO:6), $Ala^{16}$-GLP-1 (7-36) (SEQ ID NO:7), $Glu^{22}$-GLP-1 (7-36) (SEQ ID NO:8), $His^{23}$-GLP-1 (7-36) (SEQ ID NO:9), $Glu^{24}$-GLP-1 (7-36) (SEQ ID NO:10), $Trp^{26}$-GLP-1 (7-36) (SEQ ID NO:11), $Ala^{27}$-GLP-1 (7-36) (SEQ ID NO:12), $Glu^{30}$-GLP-1 (7-36) (SEQ ID NO:13), $Asp^{33}$-GLP-1 (7-36) (SEQ ID NO:14), $Glu^{34}$-GLP-1 (7-36) (SEQ ID NO:15), $Thr^{35}$-GLP-1 (7-36) (SEQ ID NO:16), $Gly^8$-$Glu^{24}$-GLP-1 (7-36) (SEQ ID NO:17), and $Leu^8$-$Ala^{33}$-GLP-1 (7-36) (SEQ ID NO:18).

With regard to the method of producing GLP-1 (7-36) and GLP-1 analogs, the recombinant methods of the present invention have a number of advantages over other methods. Chemical synthesis of GLP-1, for example, is technically demanding, and the cost of such synthesis is high. Furthermore, standard methods to produce recombinant GLP-1 by genetic engineering currently yield little success, due to a variety of problems normally associated with such techniques.

For example, the direct expression in a host cell of a polypeptide consisting of 20 to 60 amino acid residues is not feasible because such polypeptides are easily degraded. While the fusion of such a polypeptide with a carrier protein to form insoluble inclusion bodies results in little degradation, such polypeptides, under most circumstances, only represent ten percent of the fusion protein in terms of yield. Furthermore, after expression of the fusion protein, separation and purification of inclusion bodies are conducted, followed by cleavage of fusion protein, generally with cyanogen bromide in 70% formic acid solution. Under these conditions, the carrier protein is usually also cleaved into multiple polypeptide pieces, which result in extra processing steps and costs in the following protein separation and purification process. Finally, if GLP-1 $(7-36)_{NH2}$ is the desired final product, amidation has to be performed at the C-terminal end of the recombinant peptide.

Similarly, methods of producing GLP-1 such as those described in U.S. Pat. Nos. 5,512,459, 5,707,826, 6,037,143, and 6,403,361 have some major issues to be solved, e.g., the selective cleavage of the fusion protein followed by efficient purification; the requirement of dipeptide and tripeptide substrates in the transpeptidation process; and, ensuring that only the $Lys^{34}$ (and not the $Lys^{26}$) in GLP-1 (7-34)-Ala-Phe-Ala participates in transpeptidation. Therefore, such methodologies are complicated and difficult to control.

International publication WO 95/17510 (PCT/DK94/00487) discloses a method for producing GLP-1 or analog thereof in a bacterium, but the method described in WO 95/17510 is may be considered less advantageous compared to that of the present invention. First, the method of WO 95/17510 inserts into a vector an expression cassette encoding a GLP-1 precursor by using of polymerase chain reaction (PCR). As is well known, the mutation ratio in the DNA sequence will be increased with the reaction rounds of PCR. As the method of the present invention achieves the insertion by ligation of DNA fragments, such a mutation caused by PCR will not be incurred. Further, in the respect of cleaving of the precursor of GLP-1 within the host cells, it is described in the method of WO 95/17510 that protease such as Clostripain endopeptidase Arg C or trypsin may be employed. However, the price of Clostripain endopeptidase Arg C is expensive when used in the large-scale of production of GLP-1. When the protease trypsin is used to cleave the precursor, it is impossible to obtain the GLP-1 product, because the two lysine residues existing within the GLP-1 polypeptide will be also digested by trypsin, even in the condition of high pH value. In the method of the present invention, when trypsin is employed in the cleavage of the fusion protein, the lysine residue within the GLP-1 (7-36) polypeptide will be protected by acylation of the $\epsilon$-$NH_2$ group, and the protection group could be removed from the $\epsilon$-$NH_2$ group after the trypsin digestion is completed.

Finally, while recombinant methods for producing GLP-1 by attaching a signal peptide to the GLP-1 peptide in order to produce it as a secreted protein have been suggested, such methods usually yield low amounts of recombinant GLP-1.

In the present invention, hybrid sites at the two ends of the gene encoding GLP-1 (7-36) or GLP-1 analogs are used to link 1 to 32 copies of such gene in tandem. The expressed fusion protein contains multiple monomers of GLP-1 (7-36)

or GLP-1 analogs polypeptide that are specifically cleavable. This production method may greatly decrease the production cost, streamline the downstream process, and generate high yields of recombinant GLP-1 (7-36) and/or GLP-1 analogs polypeptides. The present invention therefore makes it possible to provide large quantities of GLP-1 (7-36) to the clinic, where evidence suggests that this compound or analogs thereof are cost-effective remedies for type II diabetes mellitus patients.

The present invention is further illustrated by the following examples, which should not be construed as limiting, but are merely exemplary in nature.

EXAMPLE 1

Constructing a Genetically Engineered Bacterial Strain Containing One Copy of GLP-1 (7-36) Gene Four DNA fragments are designed according to the amino acid sequence of GLP-1 (7-36) after selection of codons that are frequently used by *E. coli*. The codon for Arg is added to the 5' terminal of the GLP-1 (7-36) gene in order to create the cleavage site of the resulting fusion protein. At the 5' and 3' terminal, cleavage sites for restrictive endonucleases Bgl II and BamH I are introduced respectively, and thus complementary cohesive ends arise from restriction digestion of Bgl II and BamH I, which facilitate ligation of DNA fragments in tandem. The construction process to create the expression plasmid containing one copy of GLP-1 (7-36) gene is depicted in FIG. 1.

1. The Synthesis of DNA Fragments

The four fragments are synthesized with ABI 3900® DNA synthesizer (Applied Biosystems). The fragment sequences are shown respectively as follows:

```
         EcoR I   Bgl II      Arg
(1):  5'-AAT TCC AGA TCT ATG CGT CAC GCG GAA GGT ACC TTC ACC    (SEQ ID NO: 19)
         AGC GAT GTG AGC AGC TAT CTG -3'

(2):  5'-ACC TTC CAG ATA GCT GCT CAC ATC GCT GGT GAA GGT ACC    (SEQ ID NO: 20)
         TTC CGC GTG ACG CAT AGA TCT GG -3'

(3):  5'-GAA GGT CAG GCG GCG AAA GAA TTT ATC GCG TGG CTG GTG    (SEQ ID NO: 21)
         AAA GGT CGT GGA TCC TAG A -3'

Hind III   BamH I
(4):  5'-AG  CTT CTA GGA TCC ACG ACC TTT CAC CAG CCA CGC GAT    (SEQ ID NO: 22)
         AAA TTC TTT CGC CGC CTG -3'
```

Figure 2:
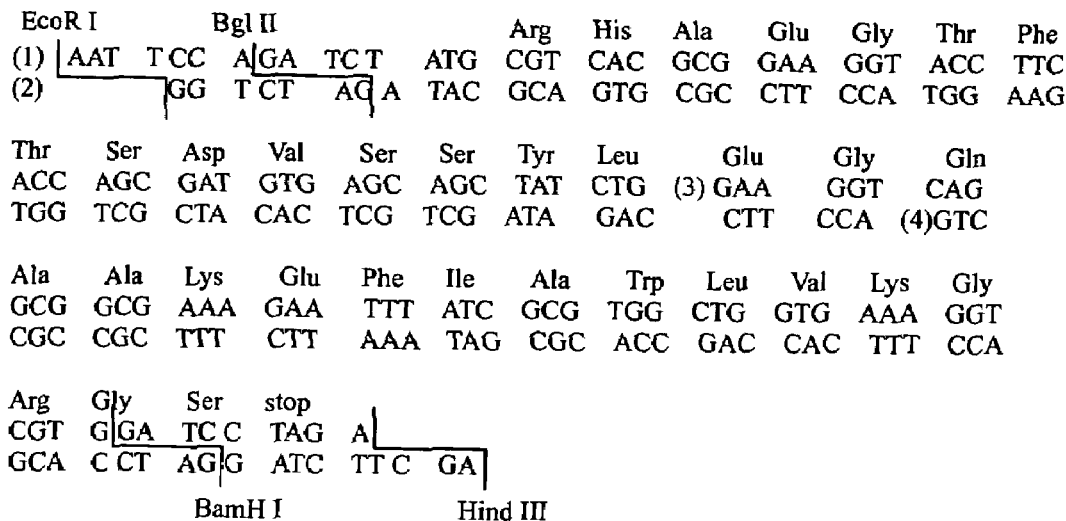
FIG. 2 shows the resulting DNA sequence encoding GLP-1 (7-36) polypeptide after ligation of fragments (1) (SEQ ID NO:19), (2) (SEQ ID NO:20), (3) (SEQ ID NO:21) and (4) (SEQ ID NO:22).

Referring to FIG. 2, fragment (1) (SEQ ID NO:19) contains at its 5' terminal the sites that can be recognized by EcoR I (restriction enzyme site A) and Bgl II (restriction enzyme site C), and contains a codon CGT encoding Arg. Fragment (2) (SEQ ID NO:20) has the sequence which is complementary to that of fragment (1). Fragment (4) (SEQ ID NO:22) contains the sites that can be recognized by Hind III (restriction enzyme site D) and BamH I (restriction enzyme site B) at its 5' terminal. Fragment (3) (SEQ ID NO:21) has the sequence which is complementary to that of fragment (4). The site AGA TCT recognized by Bgl II in fragment (1) can be interchanged with CGA TCC as recognized by BamH I in fragment (4).

2. Ligate the DNA Fragments to Form One Copy of GLP-1 (7-36) Gene.

The ligation is performed as described in "Molecular Cloning" (2$^{nd}$ Ed. by Sambrook et. al., published by Cold Spring Harbor Press). The following is a brief description:

As depicted in FIG. 1, the four DNA fragments (each content: $A_{260nm}$=5) were dissolved in 50 μl of double distilled water in four micro-centrifuge tubes respectively, the four tubes were correspondingly marked as No. 1, No. 2, No. 3 and No. 4. 1 μl of solution from No. 1 and 2 tubes were respectively removed into a 1.5 ml micro-centrifuge tube and mixed. Similarly, 1 μl of solution from No. 3 and No. 4 were respectively pipetted and mixed in another micro-centrifuge tube. 1 μl of 10× polynucleotide kinase buffer, 1 μl of 1 mM ATP and 1 μl of polynucleotide kinase were added into the two tubes respectively. The tubes were incubated at 37° C. for an hour, followed by incubation at 90° C. for five minutes to deactivate the kinase. Then the tubes were gradually cooled down to room temperature (RT). The contents within these two tubes were mixed with the addition of 1 μl of 1 mM ATP, 1 μl of 10×T$_4$DNA ligase buffer and 1 μl of T$_4$DNA ligase. The mixture was incubated at 16° C. overnight. The completion of ligation was verified by checking the fragment size on 1% agarose gel staining with ethidium bromide (EB).

3. Cloning GLP-1 (7-36) Gene into an Expression Vector.

pKK223-3 plasmid (Amersham Pharmacia Biotech) was first double digested with EcoR I and Hind III under the proper conditions. Then phenol-chloroform was added and aqueous phase was washed twice with chloroform. The digested plasmid DNA was precipitated by isopropanol at RT for an hour before centrifugation. The organic solvent in the precipitate was removed by vaporization.

The ligated GLP-1 (7-36) gene was mixed with the double digested plasmid solution followed by addition of 1 μl of 1 mM ATP, 1 μl of 10×T$_4$ DNA ligase buffer and 1 μl of T$_4$DNA ligase. The mixture was incubated at 18° C. overnight.

4. Transformation

A single JM103 colony was chosen and then cultivated in 50 ml of LB liquid medium at 37° C. until the spectrum absorption at 600 nm ($A_{600nm}$) of bacterial culture reached 0.6. After centrifugation of liquid bacterial culture, the bacterial mass was harvested and then suspended in 10 ml of ice-cooled CaCl$_2$ solution (CaCl$_2$ 60 mM, glycerol 15%, 10 mM PIPES, pH7.0). The suspension was centrifuged at 3000 rpm and the bacterial mass was resuspended in 2 ml of ice-cooled CaCl$_2$ solution and was kept in an ice bath for later use.

50 μl of competent cells were mixed with 5 μl of ligated plasmid. The mixture was heated at 42° C. for 2 minutes and then cooled down. After adding 100 μl of LB medium, this mixture was incubated at 37° C. for an hour. The mixture was then spread on an LB agarose plate containing 50 μg/ml ampicillin. The plate was incubated overnight at 37° C. Monocolonies appearing on the plate were picked and cultured for plasmid extraction. The resulting plasmid pG$_1$ was double digested with EcoR I and Hind III and the cloned genes were tested by electrophoresis on a 1% agarose gel.

5. DNA Sequencing Verification.

The DNA sequence of GLP-1 (7-36) gene carried by the recombinant plasmid was analyzed by ABI PRISM® 310 automated sequencer (Applied Biosystems). The analysis result is identical to the one as shown in FIG. 2.

EXAMPLE 2

Constructing a Genetically Engineered Bacterial Strain Containing One Copy of GLP-1 (7-36) Gene After replacement of the Bgl II site in fragment (1) of Example 1 with the Sal I site, fragment (1') (SEQ ID NO:23) was synthesized. Similarly, fragment (4') (SEQ ID NO:26) was synthesized after replacement of the BamH I site in fragment (4) of Example 1 with the Xho I site. The sequence of fragment (2') (SEQ ID NO:24) is complimentary to that of fragment (1'), while the sequence of fragment (3') (SEQ ID NO:25) is complimentary to that of fragment (4'). The sequences of fragment (1') and (4') are as follows:

```
          EcoRI    SalI          Arg
(1'): 5'- AAT TCC  GTC GAC  ATG  CGT  CAC GCG GAA GGT ACC TTC ACC    (SEQ ID NO: 23)
          AGC GAT GTG AGC AGC TAT CTG -3'

HindIII       XhoI
(4'): 5'- AG CTT  CTA  CTC GAG  ACG ACC TTT CAC CAG CCA CGC GAT    (SEQ ID NO: 26)
          AAA TTC TTT CGC CGC CTG -3'
```

Figure 3:
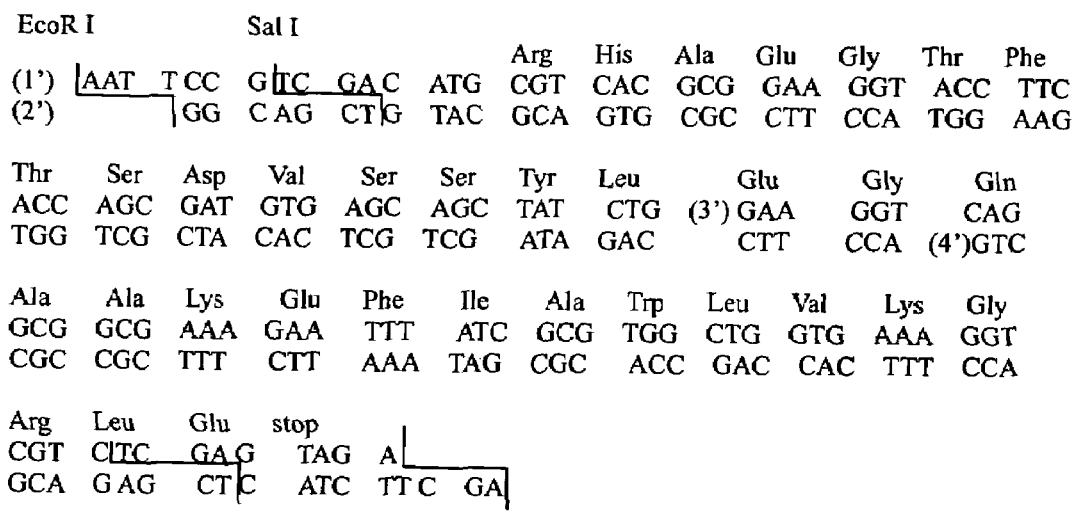
FIG. 3 shows the resulting DNA sequence encoding GLP-1 (7-36) polypeptide after ligation of fragments (1') (SEQ ID NO:23), (2') (SEQ ID NO:24), (3') (SEQ ID NO:25) and (4') (SEQ ID NO:26).

According to the procedures described in Example 1, ligation of the four fragments, digestion of the vector, insertion of the GLP-1 (7-36) gene, transformation of the expression vector (into *E. coli* JM109) and analysis of the DNA sequence were performed. The analysis result is in accordance with the one as shown in FIG. 3.

EXAMPLE 3

Constructing a Genetically Engineered Bacterial Strain Containing One Copy of GLP-1 (7-36) Gene Replace Arg codon in fragment (1) in Example 1 with Met codon to synthesize fragment (1") (SEQ ID NO:27). The sequence of fragment (2") (SEQ ID NO:28) is complementary to that of (1"). The sequences of fragment (3) and fragment (4) remain the same. The sequences of (1") and (2") are shown below:

```
           EcoR I    Bgl II      Met
(1"): 5'-  AAT TCC  AGA TCT ATG  ATG  CAC GCG GAA GGT ACC TTC ACC    (SEQ ID NO: 27)
           AGC GAT GTG AGC AGC TAT CTG -3'

(2"): 5'-  ACC TTC CAG ATA GCT GCT CAC ATC GCT GGT GAA GGT ACC TTC    (SEQ ID NO: 28)
           CGC GTG CAT CAT AGA TCT GG -3'
```

Digestion of the vector, insertion of the GLP-1 (7-36) gene, transformation of the expression vector (into *E. coli* JM109) and analysis of DNA sequence were performed as described in Example 1.

EXAMPLE 4

Figure 4:
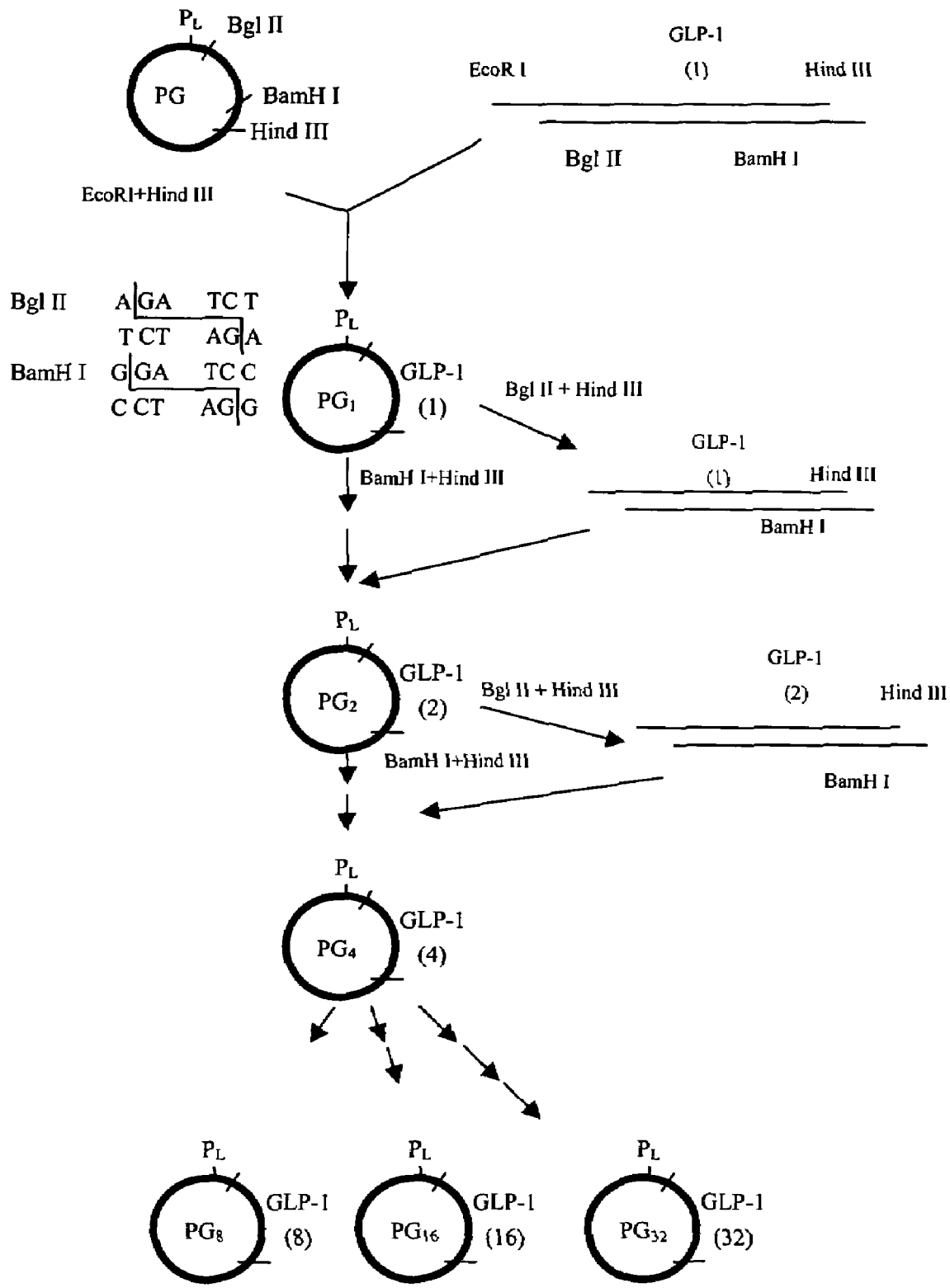
FIG. 4 depicts the process to construct a plasmid containing 2 to 32 copies of GLP-1 (7-36) genes in tandem.

Constructing a Genetically Engineered Bacterial Strain Harboring Two Copies of GLP-1 (7-36) Gene Method 1:

As shown in FIG. 4, 5 μl of the plasmid yielded in Example 1 was added into a 0.5 ml micro-centrifuge tube, and then 1 μl of 10×Bgl II buffer, 1 μl of Bgl II and 1 μl of Hind III were added to the tube respectively. The mixture was incubated at 37° C. for one hour. The released GLP-1 (7-36) gene fragment was recovered by electrophoresis on a 1% agarose gel.

1 μl of the plasmid yielded in Example 1 was mixed with 1 μl of 10×BamH I buffer, 1 μl of BamH I and 1 μl of Hind III. The mixture was incubated at 37° C. for 1 hour. Then phenol-chloroform was added and the aqueous phase was washed twice with chloroform. The digested plasmid DNA was precipitated by 60% isopropanol at RT for an hour before centrifugation. The organic solvent in the precipitate was removed by vaporization. The pellet was dissolved in 10 μl of water.

Mix the Bgl II and Hind III double digested GLP-1 (7-36) gene fragment with the Hind III and BamH I double digested plasmid. Then 1 μl of 1 mM ATP, 1 μl of 10×$T_4$ DNA ligase buffer and 2 μl of $T_4$ DNA ligase were added. The mixture was incubated overnight at 18° C.

Transform competent JM103 *E. coli* cells as described in Example 1. The bacterial suspension was then spread on a LB agarose plate containing ampicillin of 50 μg/ml. The plate was left overnight at 37° C. Single colonies appearing on the plate were picked and cultured for plasmid extraction. The resulting plasmid was double digested with EcoR I and Hind III. Select those with two copies of linked GLP-1 (7-36) gene in tandem by the electrophoresis on 1% agarose gel. The bacterial strain harboring the desired plasmid was stocked.

Method 2:

Use plasmid yielded in example 2 instead of in example 1, and substitute restriction endonucleases Bgl II and BamH I described in Method 1 with Sal I and Xho I respectively. Other procedures were performed as described in Method 1 to construct a genetically engineered bacterial strain harboring two copies of GLP-1 (7-36) gene.

Method 3:

Use the plasmid yielded from Example 3 to construct the genetically engineered bacterial strain harboring two copies of GLP-1 (7-36) gene. Other procedures were performed as described in Method 1.

EXAMPLE 5

Constructing a Genetically Engineered Bacterial Strain Containing 4 Copies of GLP-1 (7-36) Gene Following the procedures as described in Example 4, ligation of GLP-1 (7-36) genes in tandem was performed. Transform proper bacteria cell line with the plasmid carrying 4 copies of GLP-1 (7-36) gene and select the bacterial strain harboring an expression plasmid carrying 4 copies of GLP-1 (7-36) gene ligated in tandem.

EXAMPLE 6

Constructing a Genetically Engineered Bacterial Strain Containing 8 Copies of GLP-1 (7-36) Gene Following the procedures described in Example 4, ligation of GLP-1 (7-36) gene in tandem was performed. Transform proper bacteria cell line with the plasmid carrying 8 copies of GLP-1 (7-36) gene and select the bacterial strain harboring an expression plasmid carrying 8 copies of GLP-1 (7-36) gene ligated in tandem.

EXAMPLE 7

Constructing a Genetically Engineered Bacterial Strain Containing 12 Copies of GLP-1 (7-36) Gene Use the plasmids carrying 4 copies of GLP-1 (7-36) gene and the plasmids carrying 8 copies of GLP-1 (7-36) gene. Conduct double digestion of these two kinds of the plasmids respectively. Following the procedures as described in Example 4, perform the ligation in tandem and the plasmid carrying 12 copies of GLP-1 (7-36) gene were obtained. Transform the proper bacteria cell line with the plasmid and select the bacterial strain harboring an expression plasmid carrying 12 copies of GLP-1 (7-36) gene ligated in tandem.

EXAMPLE 8

Constructing a Genetically Engineered Bacterial Strain Containing 16 Copies of GLP-1 (7-36) Gene Following the procedures as described in Example 4, repeat the ligation of GLP-1 (7-36) gene in tandem. Transform proper bacteria cell line with the plasmid carrying 16 copies of GLP-1 (7-36) gene and select the bacterial strain harboring an expression plasmid carrying 16 copies of GLP-1 (7-36) gene ligated in tandem.

EXAMPLE 9

Constructing a Genetically Engineered Bacterial Strain Containing 32 Copies of GLP-1 (7-36) Gene Following the procedures as described in Example 4, repeat the ligation of GLP-1 (7-36) gene in tandem. Transform proper bacteria cell line with the plasmid carrying 32 copies of GLP-1 (7-36) gene and select the bacterial strain harboring an expression plasmid carrying 32 copies of GLP-1 (7-36) genes ligated in tandem.

EXAMPLE 10

The Fermentation of Genetically Engineered Bacterial Strain Harboring GLP-1 (7-36) Gene.

The fermentation of genetically engineered bacterial strain harboring GLP-1 (7-36) gene was conducted according to the method described by Aizhen Wu et. al. in "A Study of Fermentation Process of a Genetically Engineered *E. coli*" (*Chinese Journal of Biotechnology*, Vol. 12 supplement, pp 53-57, 1996).

1. Culture of Seeding Bacteria

The culture medium of seeding bacteria contains 10 g/L peptone, 5 g/L yeast extracts (from Difen, Sigma or Oxoid), 20 ml of 0.2M phosphate buffer at pH7.0 and $CaCl_2$, $Ni(NO_4)_3$, $CoCl_3$, $MgSO_4$ as well as $FeCl_3$ (each of the salt: 1 mg/L). The medium was autoclaved for 20 minutes at 120° C. After being cooled down to 37° C., ampicillin 50 mg/L, 20 ml of defoamer, 20 ml of seeding stock and 5 ml of 20% glucose were added. The pH value was adjusted to 6.8-7.2 with 2M NaOH and 2M HCl. Then fermentation was carried out.

2. Fermentation

The fermentation was conducted in a 5 L or 15 L or 150 L bioreactor (B. Braun Biostat). The conditions for fermentation were as follows: temperature of 37° C., $P_L$ 30→42° C., agitation speed of 500 rpm, pH of 6.8-7.2, ventilation of 5 L/min or 15 L/min or 150 L/min respectively, and $D_{O2}$ 50%.

3. Measurements of Bacterial Concentration During Fermentation

The bacterial concentration was measured every hour by taking 1 ml of fermentation culture. After the culture was centrifuged at 8000 rpm for 10 minutes, the supernatant was removed and the wet mass of bacterial mass was weighed. Alternatively the concentration can be measured by detecting the density at $OD_{600nm}$.

Figure 5:
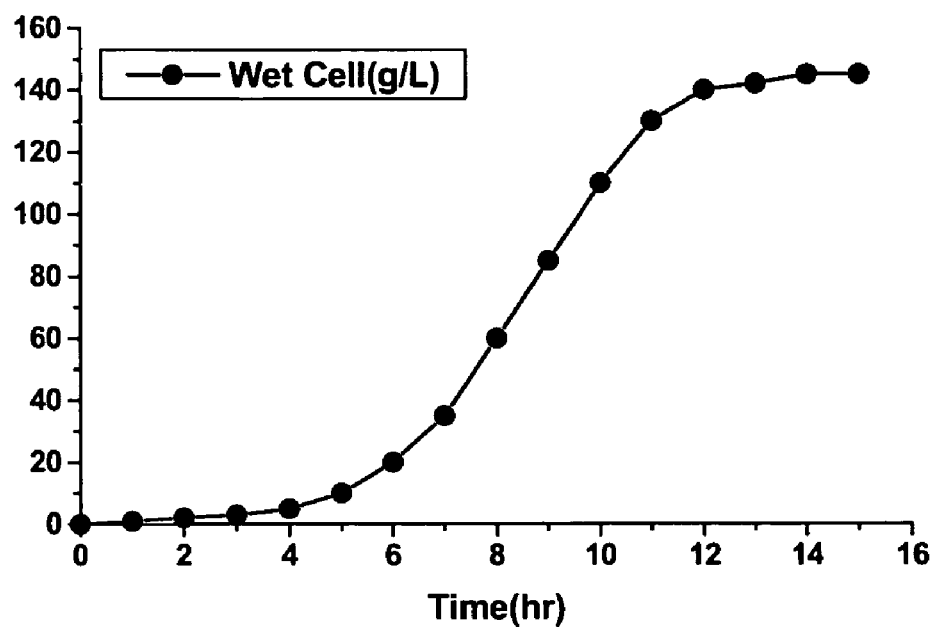
FIG. 5 shows the growth curve of genetically engineered bacterial cells during the process of fermentation.

As shown in FIG. 5, after 12-16 hours of fermentation, the density of bacteria in the fermenter was 150 g/L (wet mass). The quiescence stage was reached and the fermentation was completed.

EXAMPLE 11

The Extraction of the Inclusion Body

After fermentation, the culture medium was centrifuged at 4000 rpm. The bacterial mass was harvested and homogenized twice for disruption at a pressure of 50 MPa in a homogenizer. The cell debris suspension was centrifuged at 6000 rpm and the resulted supernatant was removed. With another round of centrifugation at 10,000 rpm, the inclusion bodies were collected and then washed twice with 20 mM of phosphate buffer (pH7.0) containing 10 mM of EDTA and 1% NaCl. After the inclusion body dissolved in 8M urea solution, the undissolved impurities were removed by centrifugation. Ultrafiltration was used to remove urea in the supernatant, and then the inclusion body was harvested with centrifugation.

EXAMPLE 12

Cleavage of the Inclusion Body

One Step Proteolysis

The inclusion bodies, which resulted from fermentation of the genetically engineered bacterium strain constructed in Examples 4 -9, can be cleaved by the following procedures.

I. Use of Clostripain Protease

Clostripain can specifically cleave the peptide bond formed by the participation of carboxyl of Arg residue.

The inclusion body yielded from Example 11 was suspended in 20 mM phosphate buffer (pH7.5). The clostripain protease was added at a ratio of 1000:1 (protein dry weight: the amount of clostripain). The mixture was incubated at 37° C. and continuously sampled and monitored by HPLC until all the inclusion bodies were completely cleaved. The impurities of large molecules were removed with ultrafiltration (molecular weight cut-off (MWCO) of 10,000). GLP-1 (7-36) was purified with preparation-scale HPLC and lyophilized to yield the desired peptide with over 99% purity.

II: Use of Trypsin Protease

Pancreatic protease trypsin can cleave the peptide bond formed by the participation of carboxyl of Lys residue or Arg residue. In the fusion protein which contains 2, 4, 8 (SEQ ID NO.29), 16 or 32 (SEQ ID NO.30) copies of GLP-1 polypeptides respectively, Lys residues within the protein were protected by anhydride. The fusion protein was digested with trypsin at pH 7-8 (the ratio of fusion protein: trypsin=1000:1 by w/w), and then was incubated at 37° C. for 2 hours. The peptide bond formed by the participation of carboxyl of Arg can be specifically cleaved by trypsin. After completion of the digestion reaction, deprotection of lysine residues was performed by using HCl of pH3.

Dissolve 200 grams (wet weight) of the inclusion bodies resulted from Example 11 into 5 litters of 20 mM $NaHCO_3$ solution with 4 gram of citraconic anhydride to conduct the acylation reaction at pH of 8.0 for 2 hours. The small molecules were removed with ultrafiltration (10,000 molecular weight cut-off "MWCO"). The trypsin was added at a ratio of 1000:1 (the protein in dry weight to the protease). The proteolytic reaction was conducted at 37° C. and monitored with HPLC till completion of the cleavage of the inclusion bodies. GLP-1 (7-36) was further purified with preparation-scale HPLC and lyophilized to yield the desired peptide with over 99% purity.

Two Step Cleavage

The inclusion bodies, which resulted from the fermentation of the genetically engineered bacterium strain constructed with Method 3 in Example 4, can be cleaved by the following method.

The inclusion body/fusion protein was dissolved in 70% formic acid or 8M urea solution to reach a concentration range of about 2-100 mg/mL (dry weight). Add cyanogen bromide (CNBr) at a mole ratio of 1:100 (fusion protein to cyanogen bromide). The mixture was stirred in the dark for 8-24 hours. Under those conditions, CNBr specifically cleaves the peptide bond formed by the carboxyl of Met. This was the first step of the two-step cleavage process.

The solution from the first cleavage was filtered with a 1000 MWCO membrane to remove small molecules. Then follow the procedures in Example 12 to conduct the second cleavage with a protease on the peptide bond formed by the carboxyl of Arg to yield GLP-1 (7-36) peptide. GLP-1 (7-36) was further purified with preparation-scale HPLC and lyophilized to yield the desired peptide with over 99% purity.

EXAMPLE 13

Chemical Analysis of GLP-1 (7-36) Polypeptide

1. Purity Analysis

Use Agilent 1100 HPLC and a Zorbax SB C18 chromatography column with an inner diameter of 4.6 mm and length of 150 mm. The mobile phase A was 0.1% TFA and the mobile phase B was 0.1% TFA/80% $CH_3CN$. A gradient of 10-80% B was formed within 20 minutes. The velocity of flow was 1 ml/min.

Figure 6:
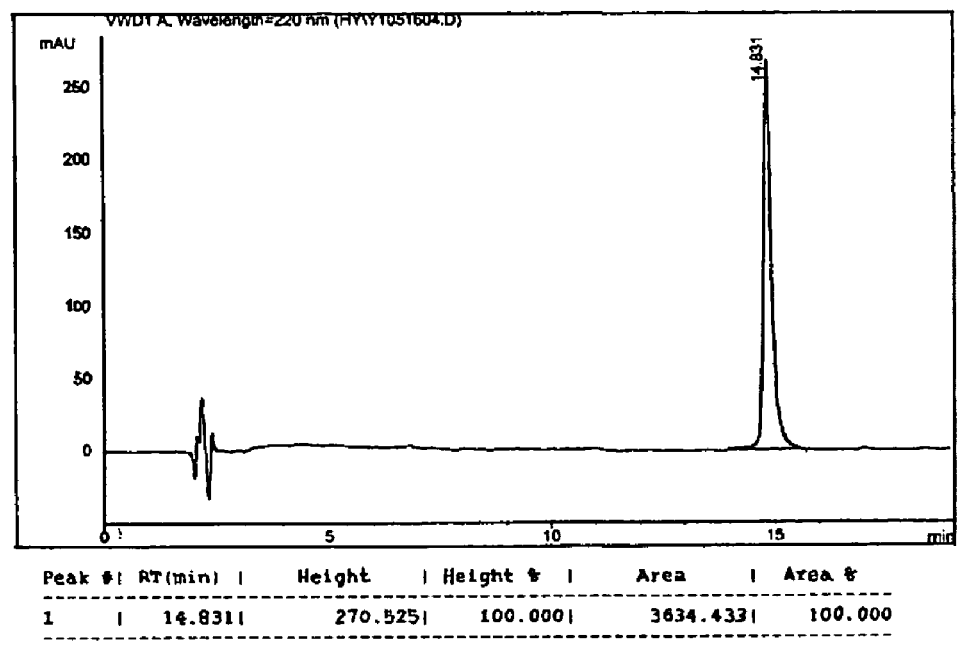
FIG. 6 shows the HPLC analysis result of the recombinant GLP-1 (7-36) polypeptide.

Dissolve 1 mg of lyophilized GLP-1 (7-36) powder (over 99% purity) in 1 ml of 0.1% TFA. Load 10 μl of the sample to the column. The result was shown in FIG. 6.

2. Amino Acid Composition Analysis

Dissolve 100 μg of GLP-1 (7-36) in 0.5 ml of 5.7 N double-distilled HCl. The resulting solution was tightly sealed in a container and incubated at 110° C. for 20 hours. Remove HCl by vacuum evaporation. Repeat the evaporation process twice with double distilled water. The volume was measured and a sample was then drawn to conduct amino acid composition analysis with Hitachi L-8800 Amino Acid Analyzer (Hitachi Scientific Instrument). The observed values were consistent with the theoretical ones, as shown in FIG. 7.

3. Mass Spectrum Analysis

Figure 8:
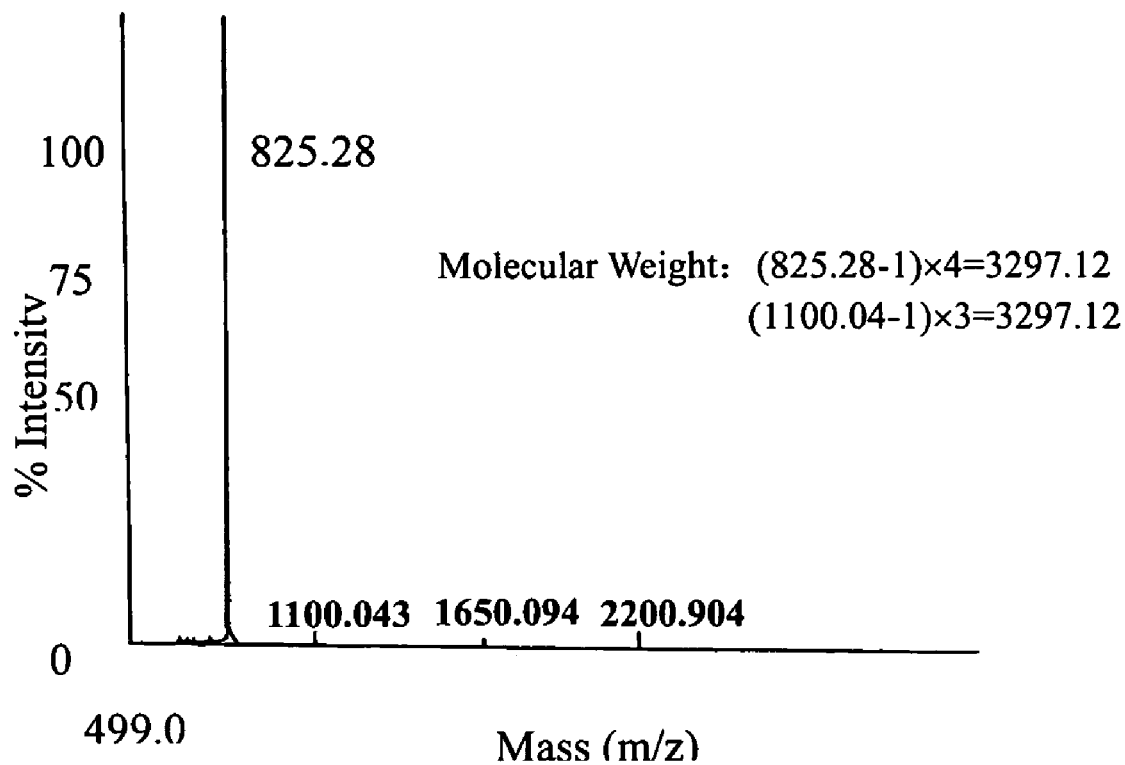
FIG. 8 shows the mass spectrum analysis results of the recombinant GLP-1 (7-36) polypeptide.

A small sample of GLP-1 (7-36) peptide was used to conduct HPLC-MS analysis with an API 2000 LC/MS/MS System (Applied Biosystems). The result was shown in FIG. 8. The GLP-1 (7-36) peptide resulting from the methodology in this invention possesses a molecular weight of 3297.12. The difference between the calculated MW of 3298.68 and the measured value was acceptable.

4. Peptide Sequence Analysis

The sample was prepared with the method describe in the above composition analysis. N-terminal peptide sequence of GLP-1 (7-36) produced thereof was determined by a Procise® cLC automated protein sequence analyzer (Applied Biosystems). The results indicate the sequence of the first 15 amino acids of GLP-1 (7-36) produced thereof was correct (this analysis was performed by the School of Life Science, Peking University).

EXAMPLE 14

The Effect of GLP-1 (7-36) on Enhancing Insulin Secretion

Healthy $C_{57}$/BL/6J mice were purchased from the Shanghai Laboratory Animal Center of Chinese Academy of Sciences. The mice were divided into three groups with 6 mice in each group. The placebo group of mice received 200 μl of saline injected into their abdominal cavity, while the testing group received 2 μg of GLP-1 (7-36) and the positive control group received 2 μg of GLP-1 (7-36)$NH_2$ (BACHEM). The moment when the animals received the injection was set as time zero. 50 μl of blood were drawn from the veins at angulus oculi with a graduated capillary which had been rinsed with heparin and then dried. The blood samples were subsequently drawn at 5, 15, 30 and 60 minutes. The blood samples were immediately mixed with 50 μl of saline in a micro-centrifuge tube. The mixture was centrifuged at 3000 rpm to remove erythrocytes. The serum was used to measure insulin concentration.

Figure 9:
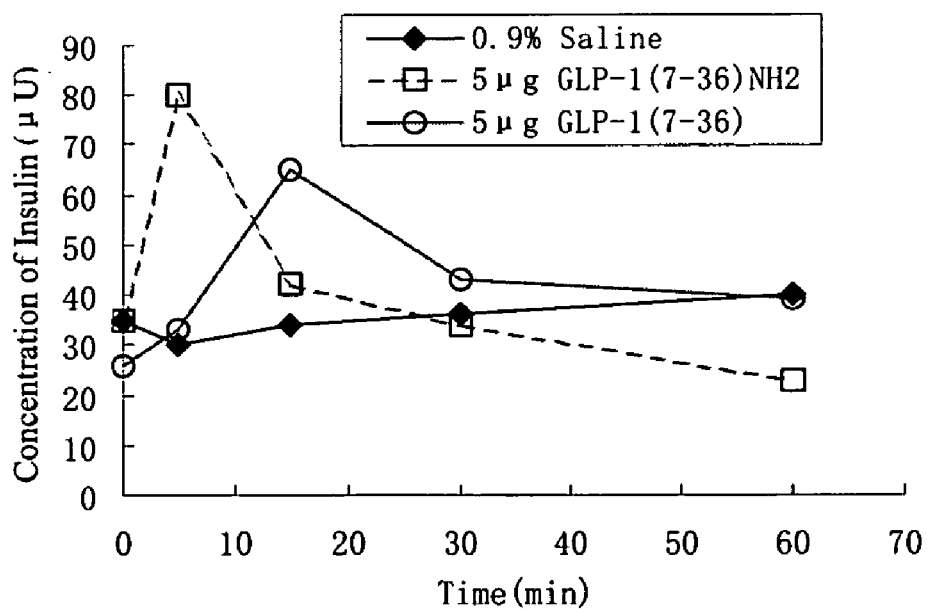
FIG. 9 shows the variation of the insulin concentration in the blood of mice after the mice were injected with GLP-1 (7-36) polypeptide.

The radioimmunoassay kit (Shanghai Institute of Biological Products, Chinese Ministry of Health) for insulin was used to measure the effect of GLP-1 (7-36) on insulin secretion. As shown in FIG. 9, there was no significant change in insulin concentration in the placebo group and the two groups receiving GLP-1 (7-36) and GLP-1 (7-36)$_{NH2}$ respectively display significant increase in serum insulin concentration. This observation indicates the administration of either GLP-1 (7-36) or GLP-1 (7-36)$_{NH2}$ enhances the secretion of insulin in mice. This result thus confirms that GLP-1 (7-36) displays a similar profile as GLP-1 (7-36)$_{NH2}$ in terms of enhancing the secretion of insulin in mice.

EXAMPLE 15

The Effect of GLP-1 (7-36) on Enhancing C-peptide Secretion

As described in Example 14, C57/BL/6J mice were divided into two groups with the placebo group receiving 200 µl of saline injected into abdominal cavity and the testing group receiving 10 µg of GLP-1 (7-36). A radioimmunoassay kit (Shanghai Institute of Biological Products, Chinese Ministry of Health) for C-peptide was used to measure the effect of GLP-1 (7-36) on C-peptide secretion.

Figure 10:
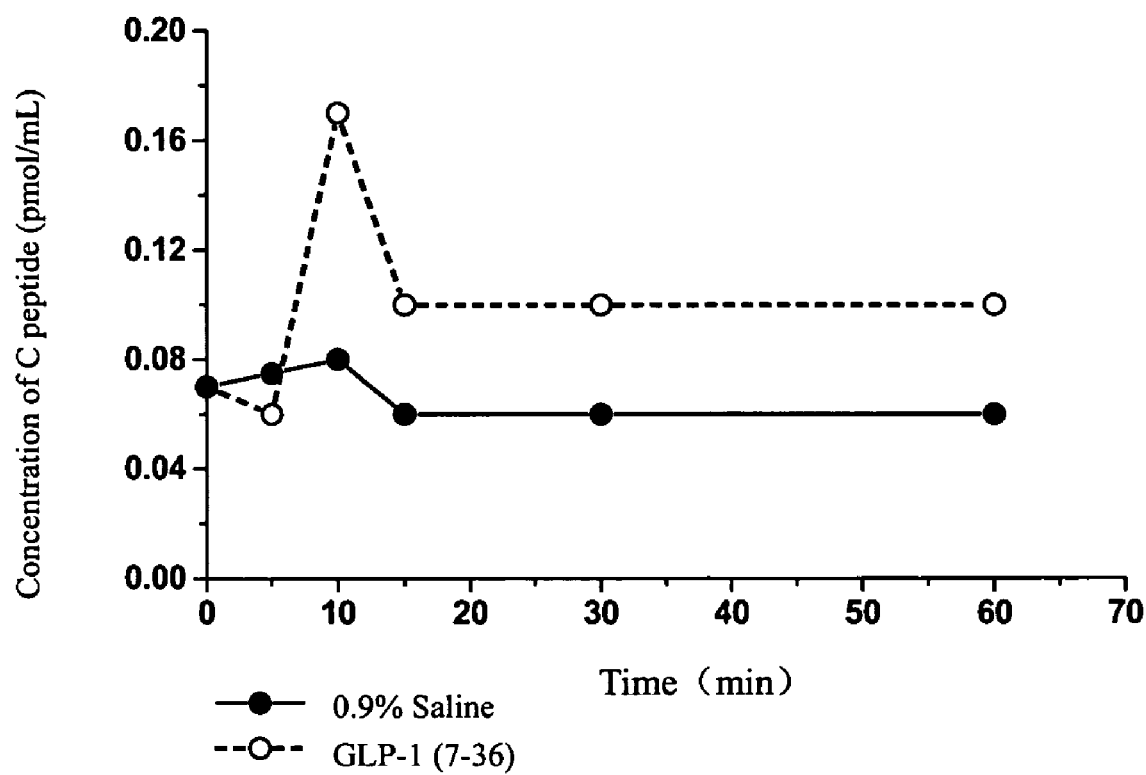
FIG. 10 shows the variation of the C-peptide concentration in the blood of mice after the mice were injected with GLP-1 (7-36) polypeptide.

As shown in FIG. 10, there was no significant change in C-peptide concentration in the placebo group and the groups receiving. GLP-1 (7-36) has displayed significant increase in serum C-peptide concentration. This observation indicates that the administration of GLP-1 (7-36) enhances the secretion of C-peptide in mice.

EXAMPLE 16

The Effect of GLP-1 (7-36) on Reducing Blood Glucose Level

Healthy $C_{57}$/BL/6J mice were purchased from Shanghai Laboratory Animal Center of Chinese Academy of Sciences. The mice were divided into four groups with 6 mice in each group. Mice fasted overnight were injected by abdominal cavity. The placebo group were injected with 200 µl of 40% glucose solution, the testing group were injected with 200 µl of 40% glucose solution plus 2 µg of GLP-1 (7-36), the positive control group(I) were injected with 200 µl of 40% glucose solution plus 2 µg of GLP-1 (7-36)$NH_2$ (Sigma), and the positive control group(II) were injected with 200 µl of 40% glucose solution plus 2 µg of GLP-1 (7-37) (Sigma). The moment when the animals received the injection was set as time zero. After the injection, 20 µl of blood sample were immediately drawn from optic sinus of each mouse with a heparin-treated capillary. The blood samples were immediately mixed with 300 µl of saline in a micro-centrifuge tube. The mixture was centrifuged at 3000 rpm to remove erythrocytes. The serum was used to measure serum glucose concentration. This procedure was repeated at the 30th, 60th and 120th minutes.

Figure 11:
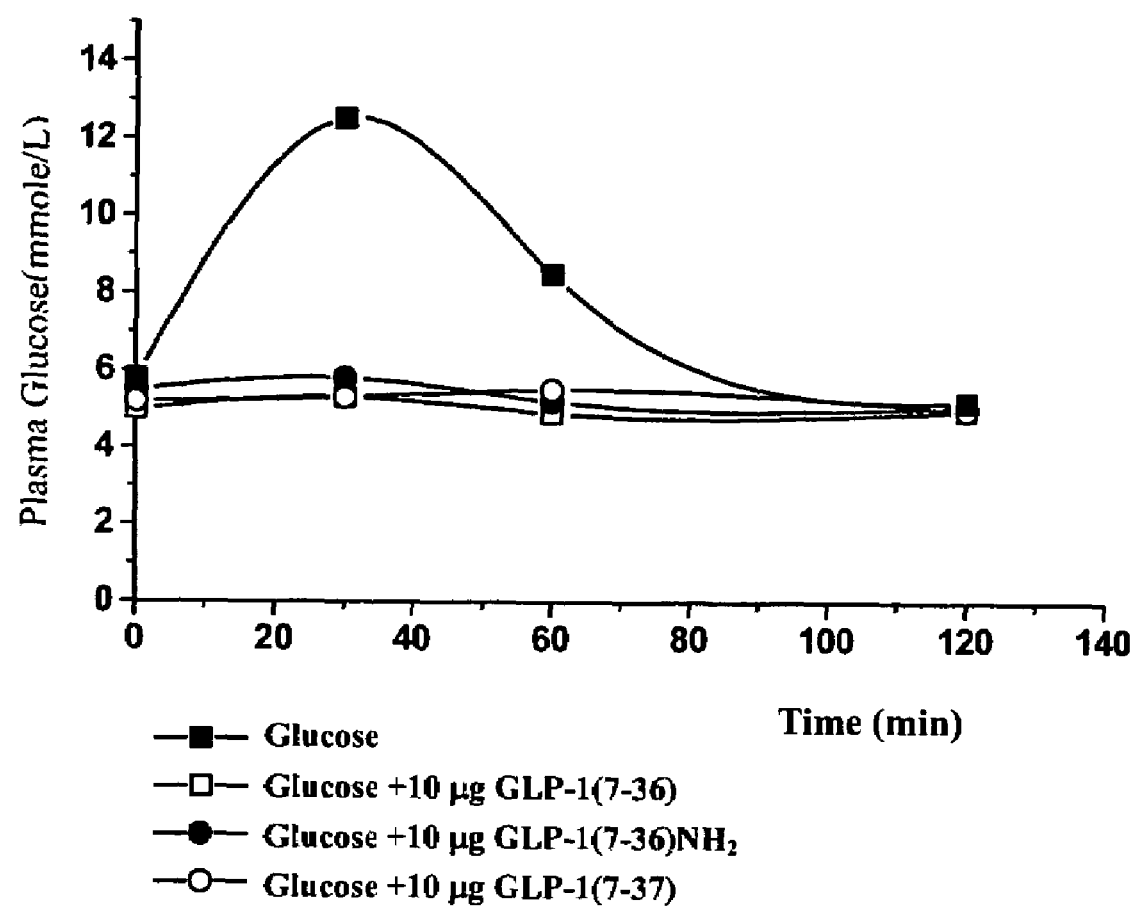
FIG. 11 shows the variation of the glucose concentration in the blood of mice after the mice were injected with GLP-1 (7-36) polypeptide.

The serum blood glucose concentration was measured by a commercial kit (Shanghai Institute of Biological Products, Chinese Ministry of Health). As shown in FIG. 11, a significant increase in the blood glucose concentration of the placebo group (injected only with glucose) and a gradual falling to the normal level has been observed. For the other three groups of mice, the serum blood glucose concentrations have no obvious rise from the normal level during the measurement process. This observation indicates that the administration of either GLP-1 (7-36), GLP-1 (7-36)$_{NH2}$ or GLP-1 (7-37) may enhance the secretion of insulin in mice to prevent dramatic fluctuation of blood glucose concentration. Therefore the results confirm that GLP-1 (7-36) displays a similar profile as GLP-1 (7-36)$_{NH2}$ or GLP-1 (7-37) in terms of lowering blood glucose.

EXAMPLE 17

Comparison of Reducing Blood Glucose Effect Between GLP-1 (7-36), GLP-1 (7-37)COOH, and GLP-1 (7-36)$NH_2$ Kun Ming mice (40 in total, male, 23 g body weight/mouse) were divided into 4 groups. After fasting for 4 hours, each mouse was injected with glucose (2 g/kg body weight) intraperitoneally. Then mice in the testing group were rejected with 50 ng/Kg of GLP-1 (7-36), GLP-1 (7-36)$_{NH2}$ (BACHEM) and GLP-1 (7-37)$_{COOH}$ (BACHEM) respectively, while mice in the control group were rejected with 0.9% NaCl saline. Blood sample was collected at the zero time and 30 minutes later for the analysis. The effect of GLP-1 (7-36), GLP-1 (7-37)$_{COOH}$, and GLP-1 (7-36)$_{NH2}$ on the reduction of blood glucose was shown in Table 1.

TABLE 1

Comparison of reducing blood glucose effect

| Groups | Blood Glucose (mmol/l) | Rate (%) |
| --- | --- | --- |
| Control | 13.75 | |
| GLP-1(7-36) | 6.51 | 50.4 |
| GLP-1(7-36)$_{NH2}$ | 8.69 | 36.8 |
| GLP-1(7-37)$_{COOH}$ | 6.77 | 50.7 |

Although the preferred embodiments and figures of this invention have been described in previous paragraphs, it should be apparent to one skilled in the art that modifications and alternative editions of this invention are possible, and substantially identical methods and substances are still within the scope of this invention, which is set forth in the following claims.

A Separate Statement to the Deposited Biological Material

1. Name and Address of the Depositary Institution:
   Name: China Committee for Culture Collection of Microorganisms General Microbiogical Culture Center
   Address: Zhong-guan-cun, Beijing, China
2. Date of the Deposit of the Biological Material with the Institution:
   Jul. 11, 2001
3. Accession Number issued by the Depositary Institution:
   CGMCC NO. 0599
4. Name and Address of the Applicant
   Name: Shanghai Hua-Yi Bio-Tech Lab
   Address: No. 36 Caobao Road, Shanghai, China

We claim:

1. A method of producing insulinotropic GLP-1 (7-36) polypeptide and/or GLP-1 analogs comprising:
   (a) introducing into a DNA fragment first and second individual restriction endonuclease cleavage sites capable of forming a hybrid site to two terminals of a gene which encodes either the GLP-1 (7-36) polypeptide or GLP-1 analogs, respectively, and a third restriction endonuclease cleavage site located outside of the region between said first and second restriction endonuclease cleavage sites, wherein the second restriction endonuclease cleavage site is located between the first and third restriction endonuclease cleavage sites;
   (b) digesting the DNA fragment of step (a) with restriction endonucleases at the first and third restriction endonuclease cleavage sites and ligating said digested DNA fragment with a vector, wherein said vector has the second and third restriction endonuclease cleavage sites and is digested at said second and third restriction endonuclease cleavage sites before said ligation;
   (c) repeating step (b) to form an expression vector comprising N copies of GLP-1 (7-36) gene, GLP-1 analog gene, or a combination of GLP-1 (7-36) gene and GLP-1 analog genes, wherein N is an integer from 2 to 32;
   (d) transforming said expression vector into a host cell;
   (e) expressing in the host cell a protein comprising N copies of the GLP-1 (7-36) polypeptide, GLP-1 analog, or the combination thereof, but without any carrier protein;
   (f) breaking up the host cell and cleaving said protein of step (e) under conditions wherein the cleavage does not occur at the peptide bonds adjacent to internal lysine residues to obtain GLP-1 (7-36) polypeptides or GLP-1 analogs that are capable of stimulating the secretion of insulin; and
   (g) separating and purifying said GLP-1 (7-36) polypeptides or GLP-1 analogs.

2. The method according to claim 1 wherein the two restriction endonucleases capable of forming a hybrid site are Bgl II and BamH I.

3. The method according to claim 1 wherein the two restriction endonucleases capable of forming a hybrid site are Sal I and Xho I.

4. The method according to claim 1 in which said vector contains N copies of the GLP-1 (7-36) gene, GLP-1 analog gene, or a combination of GLP-1 (7-36) gene and GLP-1 analog gene, wherein N is 4.

5. The method according to claim 1 in which the said vector contains N copies of the GLP-1 (7-36) gene, GLP-1 analog gene, or a combination of GLP-1 (7-36) gene and GLP-1 analog gene, wherein N is an integer from 8 to 32.

6. The method according to claim 5 in which the said vector contains N copies of the GLP-1 (7-36) gene, GLP-1 analog gene, or a combination of GLP-1 (7-36) gene and GLP-1 analog gene, wherein N is 16.

7. The method according to claim 5 in which the said vector contains N copies of the GLP-1 (7-36) gene, GLP-1 analog gene, or a combination of GLP-1 (7-36) gene and GLP-1 analog gene, wherein N is 32.

8. The method according to claim 1 in which said host cell expresses a protein containing N copies of the GLP-1 (7-36) polypeptide, GLP-1 analog, or the combination thereof, wherein N is 4.

9. The method according to claim 8 wherein said host cell is a prokaryotic cell.

10. The method according to claim 9 wherein said host cell is *Escherichia coli* JM103, JM109, HB101, or DH5α or C600.

11. The method according to claim 1 in which said host cell expresses a protein containing N copies of the GLP-1 (7-36) polypeptide, GLP-1 analog, or the combination thereof, wherein N is an integer from 8 to 32.

12. The method according to claim 11 in which said host cell expresses a protein containing N copies of the GLP-1 (7-36) polypeptide, GLP-1 analog, or the combination thereof, wherein N is 16.

13. The method according to claim 11 in which said host cell expresses a protein containing N copies of the GLP-1 (7-36) polypeptide, GLP-1 analog, or the combination thereof, wherein N is 32.

14. The method according to claim 1 wherein said protein is cleaved at step (f) by clostripain or trypsin.

15. A method of producing insulinotropic GLP-1 (7-36) polypeptide and/or GLP-1 analogs comprising:
   (a) introducing into a DNA fragment first and second individual restriction endonuclease cleavage sites capable of forming a hybrid site to two terminals of a gene which encodes either the GLP-1 (7-36) polypeptide or GLP-1 analogs, respectively, and a third restriction endonuclease cleavage site located outside of the region between said first and second restriction endonuclease cleavage sites, wherein the second restriction endonuclease cleavage site is located between the first and third restriction endonuclease cleavage sites;
   (b) digesting the DNA fragment of step (a) with restriction endonucleases at the first and third restriction endonuclease cleavage sites and ligating said digested DNA fragment with a vector, wherein said vector has the second and third restriction endonuclease cleavage sites and is digested at said second and third restriction endonuclease cleavage sites before said ligation;
   (c) repeating step (b) to form an expression vector comprising N copies of GLP-1 (7-36) gene, GLP-1 analog gene, or a combination of GLP-1 (7-36) gene and GLP-1 analog genes, wherein N is an integer from 2 to 32;

(d) transforming said expression vector into a host cell;
(e) expressing in the host cell a protein comprising N copies of the GLP-1 (7-36) polypeptide, GLP-1 analog, or the combination thereof, but without any carrier protein;
(f) breaking up the host cell and cleaving said protein of step (e) under conditions wherein the cleavage does not occur at the peptide bonds adjacent to internal lysine residues to obtain GLP-1 (7-36) polypeptides or GLP-1 analogs that are capable of stimulating the secretion of insulin.

* * * * *

UNITED STATES PATENT AND TRADEMARK OFFICE
CERTIFICATE OF CORRECTION

PATENT NO. : 7,544,512 B2
APPLICATION NO. : 10/761717
DATED : June 9, 2009
INVENTOR(S) : Sun et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 573 days.

Signed and Sealed this

Seventh Day of September, 2010

David J. Kappos
*Director of the United States Patent and Trademark Office*

SEQUENCE LISTING

```
<160> NUMBER OF SEQ ID NOS: 31

<210> SEQ ID NO 1
<211> LENGTH: 30
<212> TYPE: PRT
<213> ORGANISM: homo sapiens
```

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: homo sapiens
<220> FEATURE:
<221> NAME/KEY: MOD_RES
<222> LOCATION: (30)..(30)
<223> OTHER INFORMATION: AMIDATION, Position 30 is Arg-NH2

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Artificial
<220> FEATURE:
<223> OTHER INFORMATION: This sequence contains one or more substituted
                        amino acids relative to the wild-type GLP-1
                        (7-36) sequence.

<400> SEQUENCE: 4

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 30
<212> TYPE: PRT
<213> ORGANISM: Artificial
<220> FEATURE:
<223> OTHER INFORMATION: This sequence contains one or more substituted
                        amino acids relative to the wild-type sequence.

<400> SEQUENCE: 5

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 30

```
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 6

His Ala Glu Gly Asp Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 7
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 7

His Ala Glu Gly Thr Phe Thr Ser Asp Ala Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 8
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 8

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

<210> SEQ ID NO 9
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 9

His Ala Glu Gly Thr Phe Thr Ser Asp Val Ser Ser Tyr Leu Glu Gly
1               5                   10                  15

His Ala Ala Lys Glu Phe Ile Ala Trp Leu Val Lys Gly Arg
            20                  25                  30

<210> SEQ ID NO 10
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 10

His Ala Glu Gly Thr Phe Thr Ser Asp Val Ser Ser Tyr Leu Glu Gly
1               5                   10                  15
```

Gln Glu Ala Lys Glu Phe Ile Ala Trp Leu Val Lys Gly Arg
            20                  25                  30

<210> SEQ ID NO 11
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 11

His Ala Glu Gly Thr Phe Thr Ser Asp Val Ser Ser Tyr Leu Glu Gly
1               5                   10                  15

Gln Ala Ala Trp Glu Phe Ile Ala Trp Leu Val Lys Gly Arg
            20                  25                  30

<210> SEQ ID NO 12
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 12

His Ala Glu Gly Thr Phe Thr Ser Asp Val Ser Ser Tyr Leu Glu Gly
1               5                   10                  15

Gln Ala Ala Lys Ala Phe Ile Ala Trp Leu Val Lys Gly Arg
            20                  25                  30

<210> SEQ ID NO 13
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg
            20                  25                  30

<210> SEQ ID NO 14
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Ala Trp Leu Asp Lys Gly Arg
            20                  25                  30

<210> SEQ ID NO 15
<211> LENGTH: 30
<212> TYPE: PRT
<213> ORGANISM: Artificial
<220> FEATURE:
<223> OTHER INFORMATION: This sequence contains one or more substituted
                        amino acids relative to the wild-type sequence.

```
<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Glu Gly Arg
            20                  25                  30

<210> SEQ ID NO 16
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 16

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Thr Arg
            20                  25                  30

<210> SEQ ID NO 17
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 17

His Gly Glu Gly Thr Phe Thr Ser Asp Val Ser Ser Tyr Leu Glu Gly
1               5                   10                  15

Gln Gly Ala Lys Glu Phe Ile Ala Trp Leu Val Lys Gly Arg
            20                  25                  30

<210> SEQ ID NO 18
<211> LENGTH: 30
<212> TYPE: PRT
<213> ORGANISM: artificial
<220> FEATURE:
<223> OTHER INFORMATION: This sequence contains one or more substituted
                        amino acids relative to the wild-type sequence.

<400> SEQUENCE: 18

His Leu Glu Gly Thr Phe Thr Ser Asp Val Ser Ser Tyr Leu Glu Gly
1               5                   10                  15

Gln Ala Ala Lys Glu Phe Ile Ala Trp Leu Ala Lys Gly Arg
            20                  25                  30

<210> SEQ ID NO 19
<211> LENGTH: 60
<212> TYPE: DNA
<213> ORGANISM: Artificial
<220> FEATURE:
<223> OTHER INFORMATION: GLP-1 synthetic sequence

<400> SEQUENCE: 19
aattccagat ctatgcgtca cgcggaaggt accttcacca gcgatgtgag cagctatctg     60

<210> SEQ ID NO 20
<211> LENGTH: 62
<212> TYPE: DNA
<213> ORGANISM: artificial
<220> FEATURE:
<223> OTHER INFORMATION: GLP-1 synthetic sequence
```

<400> SEQUENCE: 20
accttccaga tagctgctca catcgctggt gaaggtacct tccgcgtgac gcatagatct    60
gg                                                                   62

<210> SEQ ID NO 21
<211> LENGTH: 58
<212> TYPE: DNA
<213> ORGANISM: Artificial
<220> FEATURE:
<223> OTHER INFORMATION: GLP-1 synthetic sequence

<400> SEQUENCE: 21
gaaggtcagg cggcgaaaga atttatcgcg tggctggtga aaggtcgtgg atcctaga     58

<210> SEQ ID NO 22
<211> LENGTH: 56
<212> TYPE: DNA
<213> ORGANISM: Artificial
<220> FEATURE:
<223> OTHER INFORMATION: GLP-1 synthetic sequence

<400> SEQUENCE: 22
agcttctagg atccacgacc tttcaccagc cacgcgataa attctttcgc cgcctg       56

<210> SEQ ID NO 23
<211> LENGTH: 60
<212> TYPE: DNA
<213> ORGANISM: Artificial
<220> FEATURE:
<223> OTHER INFORMATION: GLP-1 synthetic sequence

<400> SEQUENCE: 23
aattccgtcg acatgcgtca cgcggaaggt accttcacca gcgatgtgag cagctatctg   60

<210> SEQ ID NO 24
<211> LENGTH: 62
<212> TYPE: DNA
<213> ORGANISM: Artificial
<220> FEATURE:
<223> OTHER INFORMATION: GLP-1 synthetic sequence

<400> SEQUENCE: 24
accttccaga tagctgctca catcgctggt gaaggtacct tccgcgtgac gcatgtcgac   60
gg                                                                   62

<210> SEQ ID NO 25
<211> LENGTH: 58
<212> TYPE: DNA
<213> ORGANISM: Artificial
<220> FEATURE:
<223> OTHER INFORMATION: GLP-1 synthetic sequence

<400> SEQUENCE: 25
gaaggtcagg cggcgaaaga atttatcgcg tggctggtga aaggtcgtct cgagtaga     58

<210> SEQ ID NO 26
<211> LENGTH: 56
<212> TYPE: DNA
<213> ORGANISM: Artificial
<220> FEATURE:
<223> OTHER INFORMATION: GLP-1 synthetic sequence

<400> SEQUENCE: 26

-continued

```
agcttctact cgagacgacc tttcaccagc cacgcgataa attctttcgc cgcctg         56
```

<210> SEQ ID NO 27
<211> LENGTH: 60
<212> TYPE: DNA
<213> ORGANISM: Artificial
<220> FEATURE:
<223> OTHER INFORMATION: GLP-1 synthetic sequence

<400> SEQUENCE: 27

```
aattccagat ctatgatgca cgcggaaggt accttcacca gcgatgtgag cagctatctg    60
```

<210> SEQ ID NO 28
<211> LENGTH: 62
<212> TYPE: DNA
<213> ORGANISM: Artificial
<220> FEATURE:
<223> OTHER INFORMATION: GLP-1 synthetic sequence

<400> SEQUENCE: 28

```
accttccaga tagctgctca catcgctggt gaaggtacct ccgcgtgca tcatagatct     60
gg                                                                   62
```

<210> SEQ ID NO 29
<211> LENGTH: 811
<212> TYPE: DNA
<213> ORGANISM: Artificial
<220> FEATURE:
<223> OTHER INFORMATION: This sequence contains eight copies of GLP-1
      (7-36) polypeptide
<220> FEATURE:
<221> NAME/KEY: exon
<222> LOCATION: (13)..(807)

<400> SEQUENCE: 29

```
aattccagat ct atg cgt cac gcg gaa ggt acc ttc acc agc gat gtg agc   51
              Met Arg His Ala Glu Gly Thr Phe Thr Ser Asp Val Ser
              1               5                  10 agc tat ctg gaa ggt cag gcg gcg aaa gaa ttt atc gcg tgg ctg gtg     99
Ser Tyr Leu Glu Gly Gln Ala Ala Lys Glu Phe Ile Ala Trp Leu Val
    15                  20                  25 aaa ggt cgt gga tct cgt cac gcg gaa ggt acc ttc acc agc gat gtg    147
Lys Gly Arg Gly Ser Arg His Ala Glu Gly Thr Phe Thr Ser Asp Val
30                  35                  40                  45 agc agc tat ctg gaa ggt cag gcg gcg aaa gaa ttt atc gcg tgg ctg    195
Ser Ser Tyr Leu Glu Gly Gln Ala Ala Lys Glu Phe Ile Ala Trp Leu
                50                  55                  60 gtg aaa ggt cgt gga tct cgt cac gcg gaa ggt acc ttc acc agc gat    243
Val Lys Gly Arg Gly Ser Arg His Ala Glu Gly Thr Phe Thr Ser Asp
            65                  70                  75 gtg agc agc tat ctg gaa ggt cag gcg gcg aaa gaa ttt atc gcg tgg    291
Val Ser Ser Tyr Leu Glu Gly Gln Ala Ala Lys Glu Phe Ile Ala Trp
        80                  85                  90 ctg gtg aaa ggt cgt gga tct cgt cac gcg gaa ggt acc ttc acc agc    339
Leu Val Lys Gly Arg Gly Ser Arg His Ala Glu Gly Thr Phe Thr Ser
    95                  100                 105 gat gtg agc agc tat ctg gaa ggt cag gcg gcg aaa gaa ttt atc gcg    387
Asp Val Ser Ser Tyr Leu Glu Gly Gln Ala Ala Lys Glu Phe Ile Ala
110                 115                 120                 125 tgg ctg gtg aaa ggt cgt gga tct cgt cac gcg gaa ggt acc ttc acc    435
Trp Leu Val Lys Gly Arg Gly Ser Arg His Ala Glu Gly Thr Phe Thr
                130                 135                 140 agc gat gtg agc agc tat ctg gaa ggt cag gcg gcg aaa gaa ttt atc    483
```

```
Ser Asp Val Ser Ser Tyr Leu Glu Gly Gln Ala Ala Lys Glu Phe Ile
        145                 150                 155 gcg tgg ctg gtg aaa ggt cgt gga tct cgt cac gcg gaa ggt acc ttc     531
Ala Trp Leu Val Lys Gly Arg Gly Ser Arg His Ala Glu Gly Thr Phe
        160                 165                 170 acc agc gat gtg agc agc tat ctg gaa ggt cag gcg gcg aaa gaa ttt     579
Thr Ser Asp Val Ser Ser Tyr Leu Glu Gly Gln Ala Ala Lys Glu Phe
        175                 180                 185 atc gcg tgg ctg gtg aaa ggt cgt gga tct cgt cac gcg gaa ggt acc     627
Ile Ala Trp Leu Val Lys Gly Arg Gly Ser Arg His Ala Glu Gly Thr
190                 195                 200                 205 ttc acc agc gat gtg agc agc tat ctg gaa ggt cag gcg gcg aaa gaa     675
Phe Thr Ser Asp Val Ser Ser Tyr Leu Glu Gly Gln Ala Ala Lys Glu
                210                 215                 220 ttt atc gcg tgg ctg gtg aaa ggt cgt gga tct cgt cac gcg gaa ggt     723
Phe Ile Ala Trp Leu Val Lys Gly Arg Gly Ser Arg His Ala Glu Gly
                225                 230                 235 acc ttc acc agc gat gtg agc agc tat ctg gaa ggt cag gcg gcg aaa     771
Thr Phe Thr Ser Asp Val Ser Ser Tyr Leu Glu Gly Gln Ala Ala Lys
        240                 245                 250 gaa ttt atc gcg tgg ctg gtg aaa ggt cgt gga tcc taga               811
Glu Phe Ile Ala Trp Leu Val Lys Gly Arg Gly Ser
        255                 260                 265

<210> SEQ ID NO 30
<211> LENGTH: 3187
<212> TYPE: DNA
<213> ORGANISM: Artificial
<220> FEATURE:
<223> OTHER INFORMATION: This sequence contains thirty-two copies of
      GLP-1(7-36) polypeptide
<220> FEATURE:
<221> NAME/KEY: exon
<222> LOCATION: (13)..(3183)

<400> SEQUENCE: 30
aattccagat ct atg cgt cac gcg gaa ggt acc ttc acc agc gat gtg agc     51
           Met Arg His Ala Glu Gly Thr Phe Thr Ser Asp Val Ser
           1               5                   10 agc tat ctg gaa ggt cag gcg gcg aaa gaa ttt atc gcg tgg ctg gtg       99
Ser Tyr Leu Glu Gly Gln Ala Ala Lys Glu Phe Ile Ala Trp Leu Val
        15                  20                  25 aaa ggt cgt gga tct cgt cac gcg gaa ggt acc ttc acc agc gat gtg      147
Lys Gly Arg Gly Ser Arg His Ala Glu Gly Thr Phe Thr Ser Asp Val
30                  35                  40                  45 agc agc tat ctg gaa ggt cag gcg gcg aaa gaa ttt atc gcg tgg ctg      195
Ser Ser Tyr Leu Glu Gly Gln Ala Ala Lys Glu Phe Ile Ala Trp Leu
                50                  55                  60 gtg aaa ggt cgt gga tct cgt cac gcg gaa ggt acc ttc acc agc gat      243
Val Lys Gly Arg Gly Ser Arg His Ala Glu Gly Thr Phe Thr Ser Asp
            65                  70                  75 gtg agc agc tat ctg gaa ggt cag gcg gcg aaa gaa ttt atc gcg tgg      291
Val Ser Ser Tyr Leu Glu Gly Gln Ala Ala Lys Glu Phe Ile Ala Trp
        80                  85                  90 ctg gtg aaa ggt cgt gga tct cgt cac gcg gaa ggt acc ttc acc agc      339
Leu Val Lys Gly Arg Gly Ser Arg His Ala Glu Gly Thr Phe Thr Ser
    95                  100                 105 gat gtg agc agc tat ctg gaa ggt cag gcg gcg aaa gaa ttt atc gcg      387
Asp Val Ser Ser Tyr Leu Glu Gly Gln Ala Ala Lys Glu Phe Ile Ala
110                 115                 120                 125 tgg ctg gtg aaa ggt cgt gga tct cgt cac gcg gaa ggt acc ttc acc      435
Trp Leu Val Lys Gly Arg Gly Ser Arg His Ala Glu Gly Thr Phe Thr
```

-continued

```
                        130                 135                 140
agc gat gtg agc agc tat ctg gaa ggt cag gcg gcg aaa gaa ttt atc     483
Ser Asp Val Ser Ser Tyr Leu Glu Gly Gln Ala Ala Lys Glu Phe Ile
        145                 150                 155 gcg tgg ctg gtg aaa ggt cgt gga tct cgt cac gcg gaa ggt acc ttc     531
Ala Trp Leu Val Lys Gly Arg Gly Ser Arg His Ala Glu Gly Thr Phe
160                 165                 170 acc agc gat gtg agc agc tat ctg gaa ggt cag gcg gcg aaa gaa ttt     579
Thr Ser Asp Val Ser Ser Tyr Leu Glu Gly Gln Ala Ala Lys Glu Phe
    175                 180                 185 atc gcg tgg ctg gtg aaa ggt cgt gga tct cgt cac gcg gaa ggt acc     627
Ile Ala Trp Leu Val Lys Gly Arg Gly Ser Arg His Ala Glu Gly Thr
190                 195                 200                 205 ttc acc agc gat gtg agc agc tat ctg gaa ggt cag gcg gcg aaa gaa     675
Phe Thr Ser Asp Val Ser Ser Tyr Leu Glu Gly Gln Ala Ala Lys Glu
                210                 215                 220 ttt atc gcg tgg ctg gtg aaa ggt cgt gga tct cgt cac gcg gaa ggt     723
Phe Ile Ala Trp Leu Val Lys Gly Arg Gly Ser Arg His Ala Glu Gly
            225                 230                 235 acc ttc acc agc gat gtg agc agc tat ctg gaa ggt cag gcg gcg aaa     771
Thr Phe Thr Ser Asp Val Ser Ser Tyr Leu Glu Gly Gln Ala Ala Lys
        240                 245                 250 gaa ttt atc gcg tgg ctg gtg aaa ggt cgt gga tct cgt cac gcg gaa     819
Glu Phe Ile Ala Trp Leu Val Lys Gly Arg Gly Ser Arg His Ala Glu
    255                 260                 265 ggt acc ttc acc agc gat gtg agc agc tat ctg gaa ggt cag gcg gcg     867
Gly Thr Phe Thr Ser Asp Val Ser Ser Tyr Leu Glu Gly Gln Ala Ala
270                 275                 280                 285 aaa gaa ttt atc gcg tgg ctg gtg aaa ggt cgt gga tct cgt cac gcg     915
Lys Glu Phe Ile Ala Trp Leu Val Lys Gly Arg Gly Ser Arg His Ala
                290                 295                 300 gaa ggt acc ttc acc agc gat gtg agc agc tat ctg gaa ggt cag gcg     963
Glu Gly Thr Phe Thr Ser Asp Val Ser Ser Tyr Leu Glu Gly Gln Ala
            305                 310                 315 gcg aaa gaa ttt atc gcg tgg ctg gtg aaa ggt cgt gga tct cgt cac    1011
Ala Lys Glu Phe Ile Ala Trp Leu Val Lys Gly Arg Gly Ser Arg His
        320                 325                 330 gcg gaa ggt acc ttc acc agc gat gtg agc agc tat ctg gaa ggt cag    1059
Ala Glu Gly Thr Phe Thr Ser Asp Val Ser Ser Tyr Leu Glu Gly Gln
    335                 340                 345 gcg gcg aaa gaa ttt atc gcg tgg ctg gtg aaa ggt cgt gga tct cgt    1107
Ala Ala Lys Glu Phe Ile Ala Trp Leu Val Lys Gly Arg Gly Ser Arg
350                 355                 360                 365 cac gcg gaa ggt acc ttc acc agc gat gtg agc agc tat ctg gaa ggt    1155
His Ala Glu Gly Thr Phe Thr Ser Asp Val Ser Ser Tyr Leu Glu Gly
                370                 375                 380 cag gcg gcg aaa gaa ttt atc gcg tgg ctg gtg aaa ggt cgt gga tct    1203
Gln Ala Ala Lys Glu Phe Ile Ala Trp Leu Val Lys Gly Arg Gly Ser
            385                 390                 395 cgt cac gcg gaa ggt acc ttc acc agc gat gtg agc agc tat ctg gaa    1251
Arg His Ala Glu Gly Thr Phe Thr Ser Asp Val Ser Ser Tyr Leu Glu
        400                 405                 410 ggt cag gcg gcg aaa gaa ttt atc gcg tgg ctg gtg aaa ggt cgt gga    1299
Gly Gln Ala Ala Lys Glu Phe Ile Ala Trp Leu Val Lys Gly Arg Gly
    415                 420                 425 tct cgt cac gcg gaa ggt acc ttc acc agc gat gtg agc agc tat ctg    1347
Ser Arg His Ala Glu Gly Thr Phe Thr Ser Asp Val Ser Ser Tyr Leu
430                 435                 440                 445 gaa ggt cag gcg gcg aaa gaa ttt atc gcg tgg ctg gtg aaa ggt cgt    1395
```

```
                Glu Gly Gln Ala Ala Lys Glu Phe Ile Ala Trp Leu Val Lys Gly Arg
                            450                 455                 460 gga tct cgt cac gcg gaa ggt acc ttc acc agc gat gtg agc agc tat              1443
Gly Ser Arg His Ala Glu Gly Thr Phe Thr Ser Asp Val Ser Ser Tyr
            465                 470                 475 ctg gaa ggt cag gcg gcg aaa gaa ttt atc gcg tgg ctg gtg aaa ggt              1491
Leu Glu Gly Gln Ala Ala Lys Glu Phe Ile Ala Trp Leu Val Lys Gly
        480                 485                 490 cgt gga tct cgt cac gcg gaa ggt acc ttc acc agc gat gtg agc agc              1539
Arg Gly Ser Arg His Ala Glu Gly Thr Phe Thr Ser Asp Val Ser Ser
    495                 500                 505 tat ctg gaa ggt cag gcg gcg aaa gaa ttt atc gcg tgg ctg gtg aaa              1587
Tyr Leu Glu Gly Gln Ala Ala Lys Glu Phe Ile Ala Trp Leu Val Lys
510                 515                 520                 525 ggt cgt gga tct cgt cac gcg gaa ggt acc ttc acc agc gat gtg agc              1635
Gly Arg Gly Ser Arg His Ala Glu Gly Thr Phe Thr Ser Asp Val Ser
                530                 535                 540 agc tat ctg gaa ggt cag gcg gcg aaa gaa ttt atc gcg tgg ctg gtg              1683
Ser Tyr Leu Glu Gly Gln Ala Ala Lys Glu Phe Ile Ala Trp Leu Val
            545                 550                 555 aaa ggt cgt gga tct cgt cac gcg gaa ggt acc ttc acc agc gat gtg              1731
Lys Gly Arg Gly Ser Arg His Ala Glu Gly Thr Phe Thr Ser Asp Val
        560                 565                 570 agc agc tat ctg gaa ggt cag gcg gcg aaa gaa ttt atc gcg tgg ctg              1779
Ser Ser Tyr Leu Glu Gly Gln Ala Ala Lys Glu Phe Ile Ala Trp Leu
    575                 580                 585 gtg aaa ggt cgt gga tct cgt cac gcg gaa ggt acc ttc acc agc gat              1827
Val Lys Gly Arg Gly Ser Arg His Ala Glu Gly Thr Phe Thr Ser Asp
590                 595                 600                 605 gtg agc agc tat ctg gaa ggt cag gcg gcg aaa gaa ttt atc gcg tgg              1875
Val Ser Ser Tyr Leu Glu Gly Gln Ala Ala Lys Glu Phe Ile Ala Trp
                610                 615                 620 ctg gtg aaa ggt cgt gga tct cgt cac gcg gaa ggt acc ttc acc agc              1923
Leu Val Lys Gly Arg Gly Ser Arg His Ala Glu Gly Thr Phe Thr Ser
            625                 630                 635 gat gtg agc agc tat ctg gaa ggt cag gcg gcg aaa gaa ttt atc gcg              1971
Asp Val Ser Ser Tyr Leu Glu Gly Gln Ala Ala Lys Glu Phe Ile Ala
        640                 645                 650 tgg ctg gtg aaa ggt cgt gga tct cgt cac gcg gaa ggt acc ttc acc              2019
Trp Leu Val Lys Gly Arg Gly Ser Arg His Ala Glu Gly Thr Phe Thr
    655                 660                 665 agc gat gtg agc agc tat ctg gaa ggt cag gcg gcg aaa gaa ttt atc              2067
Ser Asp Val Ser Ser Tyr Leu Glu Gly Gln Ala Ala Lys Glu Phe Ile
670                 675                 680                 685 gcg tgg ctg gtg aaa ggt cgt gga tct cgt cac gcg gaa ggt acc ttc              2115
Ala Trp Leu Val Lys Gly Arg Gly Ser Arg His Ala Glu Gly Thr Phe
                690                 695                 700 acc agc gat gtg agc agc tat ctg gaa ggt cag gcg gcg aaa gaa ttt              2163
Thr Ser Asp Val Ser Ser Tyr Leu Glu Gly Gln Ala Ala Lys Glu Phe
            705                 710                 715 atc gcg tgg ctg gtg aaa ggt cgt gga tct cgt cac gcg gaa ggt acc              2211
Ile Ala Trp Leu Val Lys Gly Arg Gly Ser Arg His Ala Glu Gly Thr
        720                 725                 730 ttc acc agc gat gtg agc agc tat ctg gaa ggt cag gcg gcg aaa gaa              2259
Phe Thr Ser Asp Val Ser Ser Tyr Leu Glu Gly Gln Ala Ala Lys Glu
    735                 740                 745 ttt atc gcg tgg ctg gtg aaa ggt cgt gga tct cgt cac gcg gaa ggt              2307
Phe Ile Ala Trp Leu Val Lys Gly Arg Gly Ser Arg His Ala Glu Gly
750                 755                 760                 765
```

-continued

```
acc ttc acc agc gat gtg agc agc tat ctg gaa ggt cag gcg gcg aaa      2355
Thr Phe Thr Ser Asp Val Ser Ser Tyr Leu Glu Gly Gln Ala Ala Lys
            770                 775                 780 gaa ttt atc gcg tgg ctg gtg aaa ggt cgt gga tct cgt cac gcg gaa      2403
Glu Phe Ile Ala Trp Leu Val Lys Gly Arg Gly Ser Arg His Ala Glu
        785                 790                 795 ggt acc ttc acc agc gat gtg agc agc tat ctg gaa ggt cag gcg gcg      2451
Gly Thr Phe Thr Ser Asp Val Ser Ser Tyr Leu Glu Gly Gln Ala Ala
    800                 805                 810 aaa gaa ttt atc gcg tgg ctg gtg aaa ggt cgt gga tct cgt cac gcg      2499
Lys Glu Phe Ile Ala Trp Leu Val Lys Gly Arg Gly Ser Arg His Ala
815                 820                 825 gaa ggt acc ttc acc agc gat gtg agc agc tat ctg gaa ggt cag gcg      2547
Glu Gly Thr Phe Thr Ser Asp Val Ser Ser Tyr Leu Glu Gly Gln Ala
830                 835                 840                 845 gcg aaa gaa ttt atc gcg tgg ctg gtg aaa ggt cgt gga tct cgt cac      2595
Ala Lys Glu Phe Ile Ala Trp Leu Val Lys Gly Arg Gly Ser Arg His
                850                 855                 860 gcg gaa ggt acc ttc acc agc gat gtg agc agc tat ctg gaa ggt cag      2643
Ala Glu Gly Thr Phe Thr Ser Asp Val Ser Ser Tyr Leu Glu Gly Gln
            865                 870                 875 gcg gcg aaa gaa ttt atc gcg tgg ctg gtg aaa ggt cgt gga tct cgt      2691
Ala Ala Lys Glu Phe Ile Ala Trp Leu Val Lys Gly Arg Gly Ser Arg
        880                 885                 890 cac gcg gaa ggt acc ttc acc agc gat gtg agc agc tat ctg gaa ggt      2739
His Ala Glu Gly Thr Phe Thr Ser Asp Val Ser Ser Tyr Leu Glu Gly
    895                 900                 905 cag gcg gcg aaa gaa ttt atc gcg tgg ctg gtg aaa ggt cgt gga tct      2787
Gln Ala Ala Lys Glu Phe Ile Ala Trp Leu Val Lys Gly Arg Gly Ser
910                 915                 920                 925 cgt cac gcg gaa ggt acc ttc acc agc gat gtg agc agc tat ctg gaa      2835
Arg His Ala Glu Gly Thr Phe Thr Ser Asp Val Ser Ser Tyr Leu Glu
                930                 935                 940 ggt cag gcg gcg aaa gaa ttt atc gcg tgg ctg gtg aaa ggt cgt gga      2883
Gly Gln Ala Ala Lys Glu Phe Ile Ala Trp Leu Val Lys Gly Arg Gly
            945                 950                 955 tct cgt cac gcg gaa ggt acc ttc acc agc gat gtg agc agc tat ctg      2931
Ser Arg His Ala Glu Gly Thr Phe Thr Ser Asp Val Ser Ser Tyr Leu
        960                 965                 970 gaa ggt cag gcg gcg aaa gaa ttt atc gcg tgg ctg gtg aaa ggt cgt      2979
Glu Gly Gln Ala Ala Lys Glu Phe Ile Ala Trp Leu Val Lys Gly Arg
    975                 980                 985 gga tct cgt cac gcg gaa ggt acc ttc acc agc  gat gtg agc agc tat    3027
Gly Ser Arg His Ala Glu Gly Thr Phe Thr Ser  Asp Val Ser Ser Tyr
990                 995                 1000                 1005 ctg gaa ggt cag gcg  gcg aaa gaa ttt atc  gcg tgg ctg gtg aaa       3072
Leu Glu Gly Gln Ala  Ala Lys Glu Phe Ile  Ala Trp Leu Val Lys
                1010                1015                 1020 ggt cgt gga tct cgt  cac gcg gaa ggt acc  ttc acc agc gat gtg       3117
Gly Arg Gly Ser Arg  His Ala Glu Gly Thr  Phe Thr Ser Asp Val
                1025                1030                 1035 agc agc tat ctg gaa  ggt cag gcg gcg aaa  gaa ttt atc gcg tgg       3162
Ser Ser Tyr Leu Glu  Gly Gln Ala Ala Lys  Glu Phe Ile Ala Trp
                1040                1045                 1050 ctg gtg aaa ggt cgt  gga tcc taga                                    3187
Leu Val Lys Gly Arg  Gly Ser
                1055

<210> SEQ ID NO 31
<211> LENGTH: 5
```

```
<212> TYPE: PRT
<213> ORGANISM: Artificial
<220> FEATURE:
<223> OTHER INFORMATION: Additional N-terminal amino acids

<400> SEQUENCE: 31

Asp Asp Asp Asp Lys
1               5
```